US006469229B1

(12) United States Patent
Sachs et al.

(10) Patent No.: US 6,469,229 B1
(45) Date of Patent: Oct. 22, 2002

(54) INBRED MINIATURE SWINE AND USES THEREOF

(75) Inventors: David H. Sachs, Newton; Scott Arn, North Andover, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/378,684

(22) Filed: Aug. 20, 1999

Related U.S. Application Data

(60) Provisional application No. 60/097,423, filed on Aug. 20, 1998.

(51) Int. Cl.[7] .................. A01K 67/027; A01K 67/00; C12N 15/00
(52) U.S. Cl. ................. 800/17; 800/8; 800/21
(58) Field of Search .................. 800/17, 21, 22, 800/24, 25, 8; 424/93.1, 572, 577, 580, 553

(56) References Cited

FOREIGN PATENT DOCUMENTS

| WO | Wo 94/26289 | 11/1994 |
| --- | --- | --- |
| WO | WO 95/13363 | 5/1995 |
| WO | WO 97/06241 | 2/1997 |
| WO | WO 97/41863 | 11/1997 |

OTHER PUBLICATIONS

Lambrigts D et al. Transplantation 66:547–561, 1998.*
Brourard S et al. Human Immunology 60:455–468, 1999.*
Moliness TE and Fiane AE. Molecular Immunology 36:269–276, 1999.*
Seidel GE. J. Anim. Sci. 71(Suppl. 3): 26–33, 1993.*
Cameron ER. Molecular Biotechnology 7:253–265, 1997.*
Mullins JJ et al. Hypertension 22:630–633, 1993.*
Kuhholzer B et al. Proceedings of the Society for Experimental Biology and Medicine 224:240–245, 2000.*
Wolf E. et al. Journal of Biotechnology 65: 99–110, 1998.*
Moreadith and Radford (J. Mol. Med. 75:208–216, 1997.*
Seamark, Reprod. Fertil. Dev. 6: 653–657, 1994.*
Mullins LJ and Mullins JJ. J. Clin. Invest.97:1557–1560, 1996.*
Gardner RL and Brook FA. International J. of Dev. Biol. 41:235–243, 1997.*
Chapter 18 in Genetics by George P. Redei, McMillan Publishing Co., Inc., NY, 1982.
K. Christensen et al., "A note on effect of inbreeding on production traits in pigs", Anim. Prod., 1994, vol. 58, p. 298–300.
K. Christensen et al., "Joint effect of 21 marker loci and effect of realized inbreeding on growth in pigs", *Animal Science*, 1996, vol. 62, p. 541–546.
M. Fredholm et al., "Characterization of 24 porcine $(dA-dC)_{n}-(dT-dG)_{n}$ microsatellites: genotyping of unrelated animals from four breeds and linkage studies", *Mammalian Genome 1993*, vol. 4 P. 187–192.
W J. Hawthorne et al., "Characterisation of an Inbred Pig Colony", Sixteenth Sci. Meeting, Program and Abstracts for the Australian Academy of Sciences, (htt p: 11 www. medeserv. com.au/racp/tsanz/ t sm653c. htm) Apr. 1998, Abstract #25.
Sachs, David, "MHC–Homozygous Miniature Swine", Swindle, M.M. (Ed.). *Swine as Models in Biomedical Research*, Seventh Charles River International Symposium, Danvers, MA, 1992, pp. 3–15.
Yamada, K. et al., "Human anti–pig T–cell mediated cytotoxicity" *Xenotransplantation*, vol. 3, No. 2, May 1996, pp. 179–187.
Rosengard, B.R. et al., "Selective Beeding of Miniature Swine Leads To An Increased Rate Of Acceptance Of MHC–Identical, But Not Of Class I–Disparate, Renal Allografts", *Journal Of Immunology*, vol. 149, No. 3, 1992, pp. 1099–1103.

\* cited by examiner

*Primary Examiner*—Dave T. Nguyen
*Assistant Examiner*—Ram R. Shukla
(74) *Attorney, Agent, or Firm*—Hale and Dorr LLP

(57) ABSTRACT

The invention provides a swine which is homozygous for a major histocompatibility complex haplotype and at least 60% homozygous at all other genetic loci and such animal is propagatable, and a cell or an organ derived therefrom. The invention also provides a method for providing a swine which is homozygous at swine leukocyte antigens (SLA) A, B, C, DR, and DQ, and in which at least 60% of all other genetic loci are homozygous, as well as a method of inducing tolerance in a recipient mammal of a first species to a graft from a donor mammal of a second species.

2 Claims, 4 Drawing Sheets

INBRED MINIATURE SWINE AND USES THEREOF

RELATED APPLICATIONS

This application claims the benefit of a previously filed Provisional Application No. 60/097,423 filed Aug. 20, 1998, which is hereby incorporated by reference.

BACKGROUND OF THE INVENTION

The major histocompatibility complex (MHC) is a set of linked genes which code for cell surface proteins involved in transplant rejection. The MHC contains three types of genes, class I, II and III (Klein J. et al.: *Immunology*: The Science of Self-Nonself Discrimination, pp. 687, 1984, John Wiley, Somerset, N.J.).

In humans, class I genes encode polymorphic 44,000 dalton glycoprotein chains that associate with a nonpolymorphic 12,000 dalton light chain, $\beta$2-microglobulin, and which are expressed on most cells of the body. Typical class I MHC genes are involved in regulating immune to viral infections (Zinkemagal R. M. et al. (1979) *Adv. Immunol.* 27:52–72).

In humans, the class II MHC antigens are cell surface glycoproteins composed of an $\alpha$ chain of approximately 35,000 daltons and a $\beta$ chain of about 28,000 that are expressed only on subsets of immunologically active cells, such as $\beta$ lymphocytes and macrophages.

Class III MHC genes code for serum proteins such as complement (C').

The MHC loci in swine are known as the swine leukocyte antigens (SLA). In 1970, Vaiman et al., (Vaiman M. et al. (1970) *Transplantation* 10: 155–161) and Viza et al. (Viza D. et al. (1970) *Nature* 227:949–951) provided descriptions of the SLA complex. These groups developed panels of SLA typing reagents (Vaiman M. et al. (1979) *Immunogenetics* 9:353–361) by preparing antisera of defined specificity as well as by characterizing cells of known SLA type (homozygous typing cells) for use in mixed lymphocyte complex, to chromosome 7 (Geffrotin C. et al. (1984) *Ann Genet* (Parix) 27:213–219). The class I swine MHC loci are designated SLA-A,B,C. The class II swine MHC loci are designated SLA-DR, DQ. Because there are numerous genes coded by the SLA complex and because usually they are inherited as a unit, haplotype designations have been developed. For example, the SLAa haplotype codes for SLA-$A^a B^a C^a DR^a DQ^a$ alleles.

Miniature swine are a good model for organ transplantation studies because of their breeding characteristics which make them one of few large animals in which genetics can be manipulated in a reasonable time, and also because of their size which permits surgical manipulations similar to those humans.

SUMMARY OF THE INVENTION

The invention provides a genetically defined, large animal, useful, e.g., as an organ, tissue, or cell, donor, which is homozygous at swine leukocyte antigens (SLA) A, B, C, DR, and DQ, and preferably in which a sufficient number of all other genetic loci are homozygous such that an organ, tissue, or cell, from one animal can be used to prolong acceptance in a recipient, e.g., a xenorecipient, of an organ, tissue, or cell, from a second animal from a herd of such animals, or such that prolongation of acceptance (e.g., by the induction of tolerance) in a recipient, e.g., a xenorecipient, of an organ, tissue, or cell, from one animal of the herd also provides prolongation of acceptance of an organ, tissue, or cell, from a second animal of the herd.

Accordingly, the invention features, a swine, preferably a miniature swine, which is homozygous at swine leukocyte antigens (SLA) A, B, C, DR, and DQ, and in which at least 60% of all other genetic loci are homozygous. In preferred embodiments, at least 65%, 70%, 75%, 80%, 85%, 90%, 95% or more, of all other genetic loci in the swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In preferred embodiments, the swine is capable of reproduction, i.e., the animal can produce functional gametes.

In another aspect, the invention features, a cell or a preparation of such cells, from a swine, preferably a miniature swine, which is homozygous at swine leukocyte antigens (SLA) A, B, C, DR, and DQ, and in which at least 60% of all other genetic loci are homozygous.

In preferred embodiments, the swine cell is an embryonic stem cell. In other preferred embodiments, the swine cell can be a hematopoietic stem cell, e.g., a cord blood hematopoietic stem cell, a bone marrow hematopoietic stem cell, or a fetal or neonatal liver or spleen hematopoietic stem cell; a differentiated blood cell, e.g., a myeloid cell, a megakaryocyte, a monocyte, a granulocyte, an eosinophil, an erythroid cell, a lymphoid cell, such as a B e o lymphocyte or a T lymphocyte; a pluripotent hematopoietic stem cell, e.g., a hematopoietic precursor, a burst-forming units-erythroid (BFU-E), a colony forming unit-erythroid (CFU-E), a colony forming unit-megakaryocyte (CFU-Meg), a colony forming unit-granulocyte-monocyte (CFU-GM), a colony forming unit-eosinophil (CFU-Eo), or a colony forming unit-granulocyte-erythrocyte-megakaryocyte-monocyte (CFU-GEMM); a swine cell other than a hematopoietic stem cell or other blood cell; a swine thymic cell, e.g., a swine thymic stromal cell; a bone marrow stromal cell; a swine liver cell; a swine kidney cell; a swine epithelial cell; a swine muscle cell, e.g., a heart cell; or a dendritic cell or precursor thereof.

In preferred embodiments, at least 65%, 70%, 75%, 80%, 85%, 90%, 95% or more, of all other genetic loci in the swine cell are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In another aspect, the invention features, an isolated cell nucleus from a swine cell, preferably a miniature swine cell, which is homozygous at swine leukocyte antigens (SLA) A, B, C, DR, and DQ, and in which at least 60% of all other genetic loci are homozygous. In preferred embodiments, the cell nucleus is from an undifferentiated cell. In other embodiments, the cell nucleus is from a differentiated cell.

In preferred embodiments, at least 65%, 70%, 75%, 80%, 85%, 90%, 95% or more, of all other genetic loci in the swine cell nucleus are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In another aspect, the invention features, an isolated organ, or a tissue, from a swine, preferably a miniature swine, which swine is homozygous at swine leukocyte antigens (SLA) A, B, C, DR, and DQ, and in which at least 60% of all other genetic loci are homozygous.

In preferred embodiments, the organ can be an organ of the gastrointestinal tract, a liver, a kidney, a pancreas, a stomach, a spleen, or a gallbladder; a sensory organ, e.g., an eye; a lung; on organ or tissue of the circulatory system, e.g., a heart. In other preferred embodiments, the tissue can be connective tissue; epithelial tissue, e.g., skin; muscle tissue; osseous tissue; vascular tissue, e.g., a blood vessel; or occular tissue, e.g., lens tissue.

In preferred embodiments, the isolated organ or tissue is from a postnatal animal, e.g., a juvenile or adult animal, or a prenatal animal, e.g., a fetus or an embryo.

In preferred embodiments, at least 65%, 70%, 75%, 80%, 85%, 90%, 95% or more, of all other genetic loci in the swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In another aspect, the invention features, a hematopoietic stem cell preparation, e.g., a bone marrow stem cell preparation, from a swine, preferably a miniature swine, which swine is homozygous at swine leukocyte antigens (SLA) A, B, C, DR, and DQ, and in which at least 60% of all other genetic loci are homozygous.

In preferred embodiments, the hematopoietic stem cell preparation is from a postnatal animal, e.g., a juvenile or adult animal, or a prenatal animal, e.g., a fetus or an embryo.

In preferred embodiments, the preparation includes hematopoietic stem cells from cord blood, the liver, or spleen.

In preferred embodiments, the preparation is a bone marrow preparation which includes immature bone marrow cells, e.g., undifferentiated hematopoietic stem cells, in addition to other bone marrow components. In other preferred embodiments, the bone marrow preparation is composed of isolated undifferentiated hematopoietic stem cells.

In preferred embodiments, at least 65%, 70%, 75%, 80%, 85%, 90%, 95% or more, of all other genetic loci in the swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In another aspect, the invention features, a herd of swine, preferably miniature swine, in which the animals are homozygous at swine leukocyte antigens (SLA) A, B, C, DR, and DQ, and in which at least 60% of all other genetic loci are homozygous. In preferred embodiments, the herd of swine includes at least one male swine and at least one female swine capable of reproduction, e.g., at least one male and one female which can produce functional gametes.

In preferred embodiments, at least 65%, 70%, 75%, 80%, 85%, 90%, 95% or more, of all other genetic loci in the swine in the herd are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In another aspect, the invention features, a method for providing a swine, preferably a miniature swine, which is homozygous at swine leukocyte antigens (SLA) A, B, C, DR, and DQ, and in which at least 60% of all other genetic loci are homozygous. The method includes:

providing a first swine which is homozygous at swine leukocyte antigens (SLA) A, B, C, DR, and DQ but which is preferably homozygous at less than 20%, 30%. 50%, or 75% of all other loci;

(1) providing a second swine which is homozygous at swine leukocyte antigens (SLA) A, B, C, DR, and DQ, which is of the same haplotype as the first swine, but which is preferably homozygous at less than 20%, 30%. 50%, or 75% of all other loci, which is preferably not a sibling, parent or offspring of the first swine;

(2) mating the first and second swine to provide an offspring;

(3) mating the offspring to a swine which is homozygous at swine leukocyte antigens (SLA) A, B, C, DR, and DQ, which is of the same haplotype as the first swine but which is preferably homozygous at less than 20%, 30%. 50%, or 75% of all other loci, which is preferably not a sibling, parent or offspring of the offspring;

(4) repeating step (3) for at least 18 generations;

(5) performing a brother sister mating from the offspring of the final mating of step (4) to produce at least on male and one female sibling (6) performing brother sister matings form the siblings of step (5) and for at least 5 additional generations, to thereby provide a swine which is homozygous at swine leukocyte antigens (SLA) A, B, C, DR, and DQ, and in which at least 60% of all other genetic loci are homozygous.

In preferred embodiments, the swine, which is homozygous at swine leukocyte antigens (SLA) A, B, C, DR, and DQ, is mated in non brother-sister matings for at least 10, 15, 16, 17, 18, 19, 20, or 25 generations, and then mated in brother-sister matings for at least 4, 5, 6, 7, 8, 9, or 10 generations.

In preferred embodiments, at least 65%, 70%, 75%, 80%, 85%, 90%, 95% or more, of all other genetic loci in the swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In preferred embodiments, the swine is capable of reproduction, i.e., the animal can produce functional gametes.

In another aspect, the invention features, a swine, preferably a miniature swine, made by a method described herein.

In another aspect, the invention features, a method of providing a swine, preferably a miniature swine, which is homozygous at swine leukocyte antigens (SLA) A, B, C, DR, and DQ, and in which at least 60% of all other genetic loci are homozygous. The method includes mating a male swine which is homozygous at swine leukocyte antigens (SLA) A, B, C, DR, and DQ, and in which at least 60% of all other genetic loci are homozygous, with a female swine which is homozygous at swine leukocyte antigens (SLA) A, B, C, DR, and DQ, and in which at least 60% of all other genetic loci are homozygous, thereby providing a swine which is homozygous at swine leukocyte antigens (SLA) A, B, C, DR, and DQ, and in which at least 60% of all other genetic loci are homozygous.

In preferred embodiments, at least 65%, 70%, 75%, 80%, 85%, 90%, 95% or more, of all other genetic loci of one or more of and more preferably all of the swine, the male swine, and the female swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$). In particularly preferred embodiments the halotype of swine, the male swine, and the female swine are the small.

In preferred embodiments, the swine is capable of reproduction, i.e., the animal can produce functional gametes.

In another aspect, the invention features, a method of providing a swine, preferably a miniature swine, which is homozygous at swine leukocyte antigens (SLA) A, B, C, DR, and DQ, and in which at least 60% of all other genetic loci are homozygous.

The method includes: transferring swine genetic material, e.g., a cell nucleus or a set of chromosomes, e.g. a complete set of chromosomes, which is homozygous at swine leukocyte antigens (SLA) A, B, C, DR, and DQ and in which at least 60% of all other genetic loci are homozygous, to a cell, wherein the cell is capable of developing into a swine, allowing the cell to develop into a swine, thereby providing a swine which is homozygous at swine leukocyte o antigens (SLA) A, B, C, DR, and DQ, and in which at least 60% of all other genetic loci are homozygous.

In preferred embodiments, the genetic material is transferred via nuclear transfer. For example, a swine cell nucleus, e.g., a nucleus from an undifferentiated swine cell, can be fused with a second cell, e.g., an oocyte, e.g., an enucleated oocyte, such as an enucleated oocyte arrested in the metaphase of the second meiotic division, and then transferred into a recipient swine, e.g., a maternal recipient swine. The embryo resulting from the fusion of the cell nucleus and the oocyte can also be cultured, e.g., cultured to the stage of blastocyst, and then transferred to the recipient swine.

In preferred embodiments, at least 65%, 70%, 75%, 80%, 85%, 90%, 95% or more, of all other genetic loci in the swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In another aspect, the invention features, a method of providing a transgenic swine, e.g., a transgenic miniature swine. The method includes:

providing a swine, e.g., a miniature swine described herein, which is homozygous at swine leukocyte antigens (SLA) A, B, C, DR, and DQ, and in which all other genetic loci are at least 60% homozygous; and introducing a transgene into the swine, thereby preparing a transgenic swine.

In preferred embodiments the transgene encodes a xenogeneic, e.g., a human protein.

In preferred embodiments, at least 65%, 70%, 75%, 80%, 85%, 90%, 95% or more, of all other genetic loci in the swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In preferred embodiments, the swine is capable of reproduction, i.e., the animal can produce functional gametes.

In another aspect, the invention features, a genetically engineered swine cell, e.g., a cultured swine cell, a retrovirally transformed swine cell, or a cell derived from a transgenic swine, or purified preparation of such cells, which include a transgene. The swine cell is from a swine, preferably a miniature swine, e.g., a miniature swine, which is homozygous at swine leukocyte antigens (SLA) A, B, C, DR, and DQ, and in which at least 60% of all other genetic loci are homozygous.

In preferred embodiments the transgene encodes a xenogeneic, e.g., a human protein.

In yet other preferred embodiments the genetically engineered swine cell is: a swine hematopoietic stem cell, e.g., a cord blood hematopoietic stem cell, a bone marrow hematopoietic stem cell, or a fetal or neonatal liver or spleen hematopoietic stem cell; derived from differentiated blood cells, e.g. a myeloid cell, such as a megakaryocytes, monocytes, granulocytes, or an eosinophils; an erythroid cell, such as a red blood cells, e.g. a lymphoid cell, such as B lymphocytes and T lymphocytes; derived from a pluripotent hematopoietic stem cell, e.g. a hematopoietic precursor, e.g. a burst-forming units-erythroid (BFU-E), a colony forming unit-erythroid (CFU-E), a colony forming unit-megakaryocyte (CFU-Meg), a colony forming unit-granulocyte-monocyte (CFU-GM), a colony forming unit-eosinophil (CFU-Eo), or a colony forming unit-granulocyte-erythrocyte-megakaryocyte-monocyte (CFU-GEMM); a swine cell other than a hematopoietic stem cell, or other blood cell; a swine thymic cell, e.g., a swine thymic stromal cell; a bone marrow stromal cell; a swine liver cell; a swine kidney cell; a swine epithelial cell; a swine hematopoietic progenitor cell; a swine muscle cell, e.g., a heart cell; or a dendritic cell or precursor thereof.

In yet other preferred embodiments the transgenic cell is: isolated or derived from cultured cells, e.g., a primary culture, e.g., a primary cell culture of hematopoietic stem cells; isolated or derived from a transgenic animal.

In yet other preferred embodiments: the transgenic swine cell is hemizygous for the transgene; the transgenic swine cell is heterozygous for the transgene; the transgenic swine cell is homozygous for the transgene (heterozygous transgenic swine can be bred to produce offspring that are homozygous for the transgene); the transgenic swine cell includes two or more transgenes.

In another aspect, the invention features, a transgenic swine, e.g., a miniature swine, which is homozygous at swine leukocyte antigens (SLA) A, B, C, DR, and DQ, and in which at least 60% of all other genetic loci are homozygous and having cells which include a transgene.

In preferred embodiments the transgene encodes a xenogeneic, e.g., a human protein.

In yet other preferred embodiments the transgene includes a nucleic acid encoding a human peptide, e.g., a hematopoietic peptide, operably linked to: a promoter other than the one it naturally occurs with; a swine promoter, e.g., a swine hematopoietic gene promoter; a viral promoter; or an inducible or developmentally regulated promoter.

In preferred embodiments, at least 65%, 70%, 75%, 80%, 85%, 90%, 95% or more, of all other genetic loci in the transgenic swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In another aspect, the invention features, an isolated swine organ or a swine tissue from a transgenic swine, e.g., a miniature swine described herein, which is homozygous at swine leukocyte antigens (SLA) A, B, C, DR, and DQ, and in which at least 60% of all other genetic loci are homozygous, having cells which include a xenogeneic, e.g., a human, nucleic acid.

In preferred embodiments the organ is a heart, lung, kidney, pancreas, or liver.

In preferred embodiments the tissue is: thymic tissue; islet cells or islets; stem cells; bone marrow; endothelial cells; skin; or vascular tissue.

In another aspect, the invention features, a method of inducing tolerance in a recipient mammal of a first species, e.g., a human, to a graft from a donor mammal of a second species, e.g., a swine, for example, a miniature swine described herein. The method includes:

providing a donor mammal, e.g., a miniature swine, which is from a herd which is homozygous for a major histocompatibility complex haplotype and at least 60% homozygous at all other genetic loci;

introducing into the recipient mammal, tolerance inducing tissue, e.g., hematopoietic stem cells from the donor mammal, thymic tissue from the donor mammal, or a nucleic acid which encodes an MHC antigen of the donor mammal;

providing a graft from the donor mammal or from a second donor mammal from the herd; and introducing the graft into the recipient, thereby inducing tolerance in a recipient mammal of a first species to a graft from a mammal of the second species.

In another aspect, the invention features, a method of inducing tolerance in a recipient mammal of a first species, e.g., a human, to a graft from a donor mammal of a second species, e.g., a swine, for example, a miniature swine described herein. The method includes:

providing a donor mammal, e.g., a miniature swine, which is from a herd which is homozygous for a major histocompatibility complex haplotype and at least 60% homozygous at all other genetic loci;

introducing into the recipient mammal, hematopoietic stem cells from the donor mammal;

providing a graft from the donor mammal or from a second donor mammal from the herd; and introducing the graft into the recipient, thereby inducing tolerance in a recipient mammal of a first species to a graft from a mammal of the second species.

In preferred embodiments, the recipient is a primate and the donor is a swine, e.g., a miniature swine; the recipient is a human and the donor is a swine, e.g., a miniature swine.

In preferred embodiments, the donor is a swine, preferably a miniature swine, which is homozygous at swine leukocyte antigens (SLA) A, B, C, DR, and DQ, and is from a herd which at least 60% of all other genetic loci are homozygous. In other preferred embodiments, at least 65%, 70%, 75%, 80%, 85%, 90%, 95% or more, of all other genetic loci in the swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In preferred embodiments the method is practiced without T cell depletion, e.g., without the administration of thymic irradiation, or T cell depleting anti T cell antibodies.

In preferred embodiments the method includes: administering to the recipient, one or both, of an inhibitor, e.g., a blocker, of the CD40 ligand-CD40 interaction and a blocker of the CD28-B7 interaction. The CD40 ligand-CD40 pathway can be inhibited by administering an antibody or soluble receptor for the CD40 ligand or CD40, e.g., by administering CTLA4-lgG. Preferably the inhibitor binds the CD40 ligand. The CD28-B7 pathway can be inhibited by administering a soluble receptor or antibody for the CD28 or B7, e.g., an anti-B7 antibody. Preferably, the inhibitor binds B7. In preferred embodiments CTLA4-lgG and an anti-b7 antibody are administered.

In preferred embodiments the method can be practiced without the administration of hematopoietic space-creating irradiation, e.g., whole body irradiation.

In preferred embodiments the method includes administering a sufficiently large number of donor hematopoietic cells to the recipient such that, donor stem cells engraft, give rise to mixed chimerism, and induce tolerance without space-creating treatment. In preferred embodiments the number of donor hematopoietic cells is at least twice, is at least equal to, or is at least 75, 50, or 25% as great as, the number of bone marrow cells found in an adult of the recipient species. In preferred embodiments the number of donor hematopoietic stem cells is at least twice, is at least equal to, or is at least 75, 50, or 25% as great as, the number of bone marrow hematopoietic stem cells found in an adult of the recipient species. In the case where an inbred population of the donor species exists, e.g., where the donor species is miniature swine, the number of available donor cells is not limited to the number of cells which can be obtained from a single animal. Thus, in such cases, the donor cells administered to the recipient can come from more than one, e.g., from two, three, four, or more animals.

The number of donor cells administered to the recipient can be increased by either increasing the number of stem cells provided in a particular administration or by providing repeated administrations of donor stem cells.

Repeated stem cell administration can promote engraftment, mixed chimerism, and long-term deletional tolerance in graft recipients. Thus, the invention also includes methods in which multiple hematopoietic stem cell administrations are provided to a recipient. Multiple administration can substantially reduce or eliminate the need for hematopoietic space-creating irradiation. Administrations can be given prior to, at the time of, or after graft implantation. In preferred embodiments multiple administrations of stem cells are provided prior to the implantation of a graft. Two, three, four, five, or more administrations can be provided. The period between administrations of hematopoietic stem cells can be varied. In preferred embodiments a subsequent administration of hematopoietic stem cell is provided: at least two days, one week, one month, or six months after the previous administration of stem cells; when the recipient begins to show signs of host lymphocyte response to donor antigen; when the level of chimerism decreases; when the level of chimerism falls below a pre-determined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain a level of mixed chimerism sufficient to maintain tolerance to donor antigen.

When multiple stem cell administrations are given, one or more of the administrations can include a number of donor hematopoietic cells which is at least twice, is equal to, or is at least 75, 50, or 25% as great as, the number of bone marrow cells found in an adult of the recipient species; include a number of donor hematopoietic stem cells which is at least twice, is equal to, or is at least 75, 50, or 25% as great as, the number of bone marrow hematopoietic stem cells found in an adult of the recipient species.

Although the methods described herein, e.g., those in which blockers of both pathways are administered, or those in which a relatively large number of hematopoietic stem cells are administered, will often eliminate the need for other preparative steps, some embodiments include inactivating preferably graft reactive or xenoreactive, e.g., swine reactive, NK cells, of the recipient mammal. This can be accomplished, e.g., by introducing into the recipient mammal an antibody capable of binding to natural killer cells of the recipient mammal. The administration of antibodies, or other treatment to inactivate natural killer cells, can be given prior to introducing the hematopoietic stem cells into the recipient mammal or prior to implanting the graft in the recipient. This antibody can be the same or different from an antibody used to inactivate T cells.

Although the methods described herein, e.g., those in which blockers of both pathways are administered, or those in which a relatively large number of hematopoietic stem cells are administered, will often eliminate the need for other preparative steps, some embodiments include inactivating e.g., by depleting natural killer cells, T cells, preferably graft reactive or xenoreactive, e.g., swine reactive, T cells of the recipient mammal. This can be accomplished, e.g., by introducing into the recipient mammal an antibody capable of binding to T cells of the recipient mammal. The administration of antibodies, or other treatment to inactivate T cells, can be given prior to introducing the hematopoietic stem cells into the recipient mammal or prior to implanting the graft in the recipient. This antibody can be the same or different from an antibody used to inactivate natural killer cells.

Other preferred embodiments include: the step of introducing into the recipient mammal, donor species-specific stromal tissue, preferably hematopoietic stromal tissue, e.g., fetal liver or thymus. In preferred embodiments: the stromal tissue is introduced simultaneously with, or prior to, the hematopoietic stem cells; the hematopoietic stem cells are introduced simultaneously with, or prior to, the antibody.

Although the methods described herein, e.g., those in which blockers of both pathways are administered, or those in which a relatively large number of hematopoietic stem cells are administered, will often eliminate the need for other preparative steps, some embodiments include (optionally): the step of, prior to hematopoietic stem cell transplantation, creating hematopoietic space, e.g., by irradiating the recipient mammal with low dose, e.g., less than 400, preferably less than 300, more preferably less than 200 or 100 rads, whole body irradiation to deplete or partially deplete the bone marrow of the recipient. As is discussed herein this treatment can be reduced or entirely eliminated.

Other preferred embodiments include: the step of, preferably prior to hematopoietic stem cell transplantation, depleting natural antibodies from the blood of the recipient mammal. Depletion can be achieved, by way of example, by contacting the recipients blood with an epitope which absorbs performed anti-donor antibody. The epitope can be coupled to an insoluble substrate and provided, e.g., as an affinity column. E.g., an α1–3 galactose linkage epitope-affinity matrix, e.g., matrix bound linear B type VI carbohydrate, can be used to deplete natural antibodies. Depletion can also be achieved by hemoperfusing an organ, e.g., a liver or a kidney, obtained from a mammal of the donor species. (In organ hemoperfusion antibodies in the blood bind to antigens on the cell surfaces of the organ and are thus removed from the blood).

Other preferred embodiments include those in which: the same mammal of the second species is the donor of one or both the graft and the hematopoietic cells.

In preferred embodiments, the method includes the step of introducing into the recipient a graft obtained from the donor which is obtained from a different organ than the hematopoietic stem cells, e.g., a heart, pancreas, liver, or kidney.

In preferred embodiments the host or recipient is a post-natal individual, e.g., an adult, or a child.

In preferred embodiments the method further includes the step of identifying a host or recipient which is in need of a graft.

In another aspect, the invention features a method of inducing tolerance in a recipient mammal of a first species, e.g., a human, to a graft from a donor mammal of a second species, e.g., a swine, for example, a miniature swine. The method includes:
   providing a donor mammal which is from a herd which is homozygous for a major histocompatibility complex haplotype and at least 60% homozygous at all other genetic loci;
   introducing into the recipient mammal, thymic tissue from the donor mammal;
   providing a graft from the donor mammal, or from a second donor mammal from the herd; and
   introducing the graft into the recipient, thereby inducing tolerance in a recipient mammal of a first species to a graft from a mammal of the second species.

In preferred embodiments, the recipient is a primate and the donor is a swine, e.g., a miniature swine; the recipient is a human and the donor is a swine, e.g., a miniature swine.

In preferred embodiments, the donor is a swine and is from a herd which is homozygous at swine leukocyte antigens (SLA) A, B, C, DR, and DQ, and is from a herd in which at least 60% of all other genetic loci are homozygous. In other preferred embodiments, at least 65%, 70%, 75%, 80%, 85%, 90%, 95% or more, of all other genetic loci in the swine herd are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

In preferred embodiments the method is practiced without T cell depletion or inactivation, e.g., without the administration of thymic irradiation, or T cell depleting anti T cell antibodies.

In preferred embodiments the method includes: administering to the recipient, one or both, of an inhibitor, e.g., a blocker, of the CD40 ligand-CD40 interaction and a blocker of the CD28-B7 interaction. The CD40 ligand-CD40 pathway can be inhibited by administering an antibody or soluble receptor for the CD40 ligand or CD40, e.g., by administering CTLA4-lgG. Preferably the inhibitor binds the CD40 ligand. The CD28-B7 pathway can be inhibited by administering a soluble receptor or antibody for the CD28 or B7, e.g., an anti-B7 antibody. Preferably, the inhibitor binds B7. In preferred embodiments CTLA4-lgG and an anti-7 antibody are administered.

Although the methods described herein, e.g., those in which blockers of both pathways are administered, will often eliminate the need for other preparative steps, some embodiments include inactivating natural killer cells, preferably graft reactive or xenoreactive, e.g., swine reactive, NK cells, of the recipient mammal. This can be accomplished, e.g., by introducing into the recipient mammal an antibody capable of binding to natural killer cells of the recipient mammal. The administration of antibodies, or other treatment to inactivate natural killer cells, can be given prior to introducing the thymic tissue into the recipient mammal or prior to implanting the graft in the recipient. This antibody can be the same or different from an antibody used to inactivate T cells.

Although methods described herein, e.g., those in which blockers of both pathways are administered, will often eliminate the need for other preparative steps, some embodiments include inactivating, e.g., by depleting T cells, preferably graft reactive or xenoreactive, e.g., swine reactive, T cells of the recipient mammal. This can be accomplished, e.g., by introducing into the recipient mammal an antibody capable of binding to T cells of the recipient mammal. The administration of antibodies, or other treatment to inactivate T cells, can be given prior to introducing the thymic tissue into the recipient mammal or prior to implanting the graft in the recipient. This antibody can be the same or different from an antibody used to inactivate natural killer cells.

Other preferred embodiments include: the step of, preferably prior to thymic tissue transplantation, depleting natural antibodies from the blood of the recipient mammal. Depletion can be achieved, by way of example, by contacting the recipients blood with an epitope which absorbs performed anti-donor antibody. The epitope can be coupled to an insoluble substrate and provided, e.g., as an affinity column. E.g., an α1–3 galactose linkage epitope-affinity matrix, e.g., matrix bound linear B type VI carbohydrate, can be used to deplete natural antibodies. Depletion can also be achieved by hemoperfusing an organ, e.g., a liver or a kidney, obtained from a mammal of the donor species. (In organ hemoperfusion antibodies in the blood bind to antigens on the cell surfaces of the organ and are thus removed from the blood.)

Other preferred embodiments include those in which: the same mammal of the second species is the donor of one or both the graft and the thymic tissue.

In preferred embodiments, the method includes the step of introducing into the recipient a graft obtained from the donor which is obtained from a different organ than the thymic tissue, e.g., a heart, pancreas, liver, or kidney.

In preferred embodiments the host or recipient is a post-natal individual, e.g., an adult, or a child.

In preferred embodiments the method further includes the step of identifying a host or recipient which is in need of a graft.

In another aspect, the invention features a method of inducing tolerance in a recipient mammal, preferably a primate, e.g., a human, to a graft obtained from a donor mammal of a second species, e.g., a swine, e.g., a miniature swine, which graft preferably expresses an MHC antigen.

The method includes:
inserting a nucleic acid, e.g., DNA, encoding an MHC antigen into a hematopoietic stem cell, e.g., bone marrow hematopoietic stem cell, of the recipient, wherein the nucleic acid encodes an MHC antigen of a swine, e.g., a miniature swine, from a herd which is homozygous for a major histocompatibility complex haplotype and at least 60% homozygous at all other genetic loci;
allowing the MHC antigen encoding nucleic acid to be expressed in the recipient; and
preferably, implanting the graft in the recipient, wherein the graft is from an animal from the herd.

In preferred embodiments, the donor is a swine from a herd which is homozygous at swine leukocyte antigens (SLA) A, B, C, DR, and DQ, and in which at least 60% of all other do genetic loci are homozygous. In other preferred embodiments, at least 65%, 70%, 75%, 80%, 85%, 90%, 95% or more, of all other genetic loci in the swine are homozygous.

In preferred embodiments, the swine leukocyte antigens (SLA) A, B, C, DR, and DQ can be of haplotype a ($A^a$, $B^a$, $C^a$, $DR^a$, $DQ^a$), haplotype c ($A^c$, $B^c$, $C^c$, $DR^c$, $DQ^c$), haplotype d ($A^d$, $B^d$, $C^d$, $DR^d$, $DQ^d$), haplotype g ($A^g$, $B^g$, $C^g$, $DR^g$, $DQ^g$), haplotype h ($A^h$, $B^h$, $C^h$, $DR^h$, $DQ^h$), or haplotype j ($A^j$, $B^j$, $C^j$, $DR^j$, $DQ^j$).

Preferred embodiments include those in which: the cell is removed from the recipient prior to the nucleic acid insertion and returned to the recipient after the nucleic acid insertion; the nucleic acid includes a MHC class I gene, e.g., a (SLA) A, B, C gene; the nucleic acid includes a MHC class II gene, e.g., a DR or DQ gene; the nucleic acid is inserted into the cell by transduction, e.g. by a retrovirus, e.g., by a Moloney-based retrovirus; and the nucleic acid is expressed in bone marrow cells and/or peripheral blood cells of the recipient at least 14, preferably 30, more preferably 60, and most preferably 120 days, after the nucleic acid is introduced into the recipient.

In preferred embodiments the method is practiced without T cell depletion, e.g., without the administration of thymic irradiation, or T cell depleting anti T cell antibodies.

In preferred embodiments the method includes: administering to the recipient, one or both, of an inhibitor, e.g., a blocker, of the CD40 ligand-CD40 interaction and a blocker of the CD28-B7 interaction. The CD40 ligand-CD40 pathway can be inhibited by administering an antibody or soluble receptor for the CD40 ligand or CD40, e.g., by administering CTLA4-lgG. Preferably the inhibitor binds the CD40 ligand. The CD28-B7 pathway can be inhibited by administering a soluble receptor or antibody for the CD28 or B7, e.g., an anti-B7 antibody. Preferably, the inhibitor binds B7. In preferred embodiments CTLA4-lgG and an anti-7 antibody are administered.

Although the methods described herein, e.g., those in which blockers of both pathways are administered, will often eliminate the need for other preparative steps, some embodiments include inactivating natural killer cells, preferably graft reactive or xenoreactive, e.g., swine reactive, NK cells, of the recipient mammal. This can be accomplished, e.g., by introducing into the recipient mammal an antibody capable of binding to natural killer cells of the recipient mammal. The administration of antibodies, or other treatment to inactivate natural killer cells, can be given prior to introducing the hematopoietic stem cells into the recipient mammal or prior to implanting the graft in the recipient. This antibody can be the same or different from an antibody used to inactivate T cells.

Although the methods described herein, e.g., those in which blockers of both pathways are administered, will often eliminate the need for other preparative steps, some embodiments include inactivating T cells, preferably graft reactive or xenoreactive, e.g., swine reactive, T cells of the recipient mammal. This can be accomplished, e.g., by introducing into the recipient mammal an antibody capable of binding to T cells of the recipient mammal. The administration of antibodies, or other treatment to inactivate, e.g., deplete, T cells, can be given prior to introducing the hematopoietic stem cells into the recipient mammal or prior to implanting the graft in the recipient. This antibody can be the same or different from an antibody used to inactivate natural killer cells.

Preferred embodiments include (optionally): the step of, prior to engineered hematopoietic stem cell transplantation, creating hematopoietic space, e.g., by irradiating the recipient mammal with low dose, e.g., less than 400, preferably less than 300, more preferably less than 200 or 100 rads, whole body irradiation to deplete or partially deplete the bone marrow of the recipient.

Other preferred embodiments include: the step of, preferably prior to engineered hematopoietic stem cell transplantation, depleting natural antibodies from the blood of the recipient mammal. Depletion can be achieved, by way of example, by contacting the recipients blood with an epitope which absorbs performed anti-donor antibody. The epitope can be coupled to an insoluble substrate and provided, e.g., as an affinity column. E.g., an $\alpha 1-3$ galactose linkage epitope-affinity matrix, e.g., matrix bound linear B type VI carbohydrate, can be used to deplete natural antibodies. Depletion can also be achieved by hemoperfusing an organ, e.g., a liver or a kidney, obtained from a mammal of the donor species. (In organ hemoperfusion antibodies in the blood bind to antigens on the cell surfaces of the organ and are thus removed from the blood.)

In preferred embodiments, the method includes the step of introducing into the recipient a graft obtained from the donor which is obtained from a different organ than the hematopoietic stem cells, e.g., a heart, pancreas, liver, or kidney.

In preferred embodiments the host or recipient is a post-natal individual, e.g., an adult, or a child.

In preferred embodiments the method further includes the step of identifying a host or recipient which is in need of a graft.

The retroviral methods of the invention allow the reconstitution of a graft recipient's bone marrow with transgenic autologous bone marrow cells expressing a donor MHC gene. Expression of a transgenic MHC gene confers tolerance to grafts which exhibit the products of these or closely related MHC genes. Thus, these methods provide for the induction of specific transplantation tolerance by somatic transfer of MHC genes. Retroviral methods of the invention avoid the undesirable side effects of broad spectrum immune suppressants which are often used in transplantation.

In another aspect, the invention features, a method of selectively breeding animals described herein to improve or maintain fecundity of a herd. The method includes:

mating a first sow of a herd with a mate from the herd;
mating a second sow of the herd with the same or a different male from the herd;
determining which sow has higher fecundity;
mating the sow with the highest fecundity (or an offspring of said sow) to thereby improve or maintain fecundity of the herd.

A herd of the invention can be expanded by matings between males and females drawn from the herd. The zygotes which result from such matings can be allowed to develop in the female which produced the egg or eggs which were fertilized in the mating. The herd can also be expanded by implanting a zygote (wherein the zygote produced by the union of a sperm cell produced by a male of the herd with an egg produced by a female of the herd) in a foster mother. The foster mother can be from the herd or can be an animal which is not from the herd. For example, a "herd" zygote can be implanted in an outbred foster mother. This method can allow for rapid expansion of a herd. Accordingly, in another aspect, the invention features a method of expanding an inbred herd, e.g., a herd described herein. The method includes:

providing a zygote which is produced by the union of a sperm cell produced by a male of the herd with an egg produced by a female of the herd;
implanting the zygote into a foster mother, e.g., a female which is preferably not from the herd, allowing the zygote to give rise to an inbred swine, thereby expanding the herd.

"A preparation of cells", as used herein, refers to cells which are physically separated from the animal which produces them.

"An isolated nucleus", as used herein, refers to a nucleus which has been removed from the cell of its origin.

"An isolated organ", as used herein, refers to an organ or tissue which has been physically separated from the animal which produces it.

"A hematopoietic stem cell preparation, as used herein, is a population of cells which includes hematopoietic stem cells. The preparation can be pure, or it can include other cell types.

"A juvenile miniature swine, is a swine which has not reached sexual maturity.

"An adult miniature swine" is one which has reached sexual maturity.

"A herd," as used herein, refers to a group of at least one male and one female which can breed to produce fertile male and female offspring. All of the animals of a herd are homozygous at SLA loci: A, B, C, DR and DQ, and all animals in the herd are homozygous for the same allele at SLA A, B, C, DR and DQ. Thus, only one allele for each of SLA A, B, C, DR, or DQ is present in the herd. Furthermore, the herd is highly inbred at all other loci. At least 60%, and preferably at least 65%, 70%, 75%, 80%, 85%, 90%, 95%, of all other loci are homozygous and for each of their loci, all swine in the herd are homozygous for the same allele. Thus in a herd wherever at least 85% of the loci are homozygous, there is no genetic variation in the herd for at least 85% of the loci. Homozygosity can be determined, e.g., by minisatellite analysis or mathematically.

"Graft", as used herein, refers to a body part, organ, tissue, or cells. Organs such as liver, kidney, heart or lung, or other body parts, such as bone or skeletal matrix, tissue, such as skin, intestines, endocrine glands, or progenitor stem cells of various types, are all examples of grafts.

"Hematopoietic stem cell", as used herein, refers to a cell, e.g., a bone marrow cell, or a fetal liver or spleen cell, which is capable of developing into all myeloid and lymphoid lineages and by virtue of being able to self-renew can provide long term hematopoietic reconstitution. Preparations of hematopoietic cells or preparations, such as bone marrow, which include other cell types, can be used in methods of the invention. Although not wishing to be bound by theory, it is believed that the hematopoietic stem cells home to a site in the recipient mammal. The preparation should include immature cells, i.e., undifferentiated hematopoietic stem cells; these desired cells can be separated out of a preparation or a complex preparation can be administered. E.g., in the case of bone marrow stem cells, the desired primitive cells can be separated out of a preparation or a complex bone marrow sample including such cells can be used. Hematopoietic stem cells can be from fetal, neonatal, immature or mature animals. Stem cells derived from the cord blood of the recipient or the donor can be used in methods of the invention. See U.S. Pat. No. 5,192,553, hereby incorporated by reference, and U.S. Pat. No. 5,004,681, hereby incorporated by reference.

"Thymic or lymph node or thymocytes or T cell", as used herein, refers to thymocytes or T cells which are resistant to inactivation by traditional methods of T cell inactivation, e.g., inactivation by a single intravenous administration of anti-T cell antibodies, e.g., antibodies, e.g., ATG preparation.

"Thymic irradiation", as used herein, refers to a treatment in which at least half, and preferably at least 75, 90, or 95% of the administered irradiation is targeted to the thymus. Whole body irradiation, even if the thymus is irradiated in the process of delivering the whole body irradiation, is not considered thymic irradiation.

"MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes. MHC antigens in swine, e.g., miniature swine, include the products (and fragments and analogs thereof) of the SLA genes, e.g., the DRB gene.

"Hematopoietic space-creating irradiation", as used herein, refers to irradiation directed to the hematopoietic tissue, i.e., to tissue in which stem cells are found, e.g., the bone marrow. It is of sufficient intensity to kill or inactivate a substantial number of hematopoietic cells. It is often given as whole body irradiation.

"Thymic space" as used herein, is a state created by a treatment that facilitates the migration to and/or development in the thymus of donor hematopoietic cells of a type which can delete or inactivate host thymocytes that recognize donor antigens. It is believed that the effect is mediated by elimination of host cells in the thymus.

"Stromal tissue", as used herein, refers to the supporting tissue or matrix of an organ, as distinguished from its functional elements or parenchyma.

"Tolerance", as used herein, refers to an inhibition of a graft recipient's immune response which would otherwise occur, e.g., in response to the introduction of a non-self MHC antigen into the recipient. Tolerance can involve humoral, cellular, or both humoral and cellular responses. Tolerance, as used herein, refers not only to complete immunologic tolerance to an antigen, but to partial immunologic tolerance, i.e., a degree of tolerance to an antigen which is greater than what would be seen if a method of the invention were not employed. Tolerance, as used herein, refers to a donor antigen-specific inhibition of the immune system as opposed to the broad spectrum inhibition of the immune system seen with immunosuppressants.

"A blocker" as used herein, refers to a molecule which binds a member of a ligand/counter-ligand pair and inhibits the interaction between the ligand and counter-ligand or which disrupts the ability of the bound member to transduce a signal. The blocker can be an antibody (or fragment thereof) to the ligand or counter ligand, a soluble ligand (soluble fragment of the counter ligand), a soluble counter ligand (soluble fragment of the counter ligand), or other protein, peptide or other molecule which binds specifically to the counter-ligand or ligand, e.g., a protein or peptide selected by virtue of its ability to bind the ligand or counter ligand in an affinity assay, e.g., a page display system.

The term "haplotype" as used herein refers to a group of alleles from closely linked loci which are usually inherited as a unit. For example, in the MHC locus in swine the SLAa haplotype codes for the SLA-$A^a$, $B^a$, $C^a$, $DR^a$, and DQa alleles, the SLAd haplotype codes for the SLA-$A^d$, $B^d$, $C^d$, $DR^d$, and $DQ^d$ alleles, etc.

The terms "organ" and "tissue" as used herein, mean any biological material that is capable of being transplanted and include organs (especially the internal vital organs such as the heart, lung, liver, kidney, pancreas and thyroid), cornea, skin, blood vessels and other connective tissue, cells including blood and hematopoietic cells, Islets of Langerhans, brain cells and cells from endocrine and other organs and bodily fluids, all of which may be candidate for transplantation.

As used herein, the term "transgene" refers to a nucleic acid sequence (encoding, e.g., one or more class I or class II MHC proteins), which is partly or entirely heterologous, i.e., foreign, to the transgenic animal or cell into which it is introduced or which when introduced into the genome results in a change of sequence in the genome. A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, a "transgenic swine" is any swine which is homozygous at swine leukocyte antigens (SLA) A, B, C, DR, and DQ, and in which at least 60% of all other genetic loci are homozygous, and in which one or more, and preferably essentially all, of the cells of the animal include a transgene. The transgene can be introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA.

As used herein, the term "genetically engineered swine cells" refers to cells derived from a swine which is homozygous at swine leukocyte antigens (SLA) A, B, C, DR, and DQ, and in which at least 60% of all other genetic loci are homozygous, and which have been used as recipients for a recombinant vector or other transfer nucleic acid, and include the progeny of the original cell which has been transfected or transformed. Genetically engineered swine cells include cells in which transgenes or other nucleic acid vectors have been incorporated into the host cell's genome, as well as cells harboring expression vectors which remain autonomous from the host cell's genome.

As used herein, the term "propagatable" refers to animals which are capable of giving rise to viable offspring by sexual or asexual reproduction. Preferably, animals of the invention are propagatable.

The high degree of genetic uniformity characteristic of animals described herein allows for considerable advantages in terms of quality assurance. For example, any single animal is representative of the herd, i.e., the same or very similar (allow for differences of are or gender) to any other, in terms of immunogenetics, size, physiology, and health.

Genetically uniform animals described herein are useful genetic engineering. for example, a first modification, e.g., the introduction of a first transgene can be made in a first animal. A second modification, e.g., the introduction of a different second transgene, can be made in a second animal. The appropriate matings can be performed to yield an animal having both modifications. Except for the modifications, all of the modified animals, as well as non-modified animals of the herd, are highly uniform. Thus, genetically engineered modifications can be introduced by matings between modified animals, with minimal introduction of changes in the genetic background.

Other features and advantages of the invention will be apparent from the following detailed description, and from the claims.

DETAILED DESCRIPTION

The drawings are first briefly described.

Inbred Miniature Swine

Figure 1:
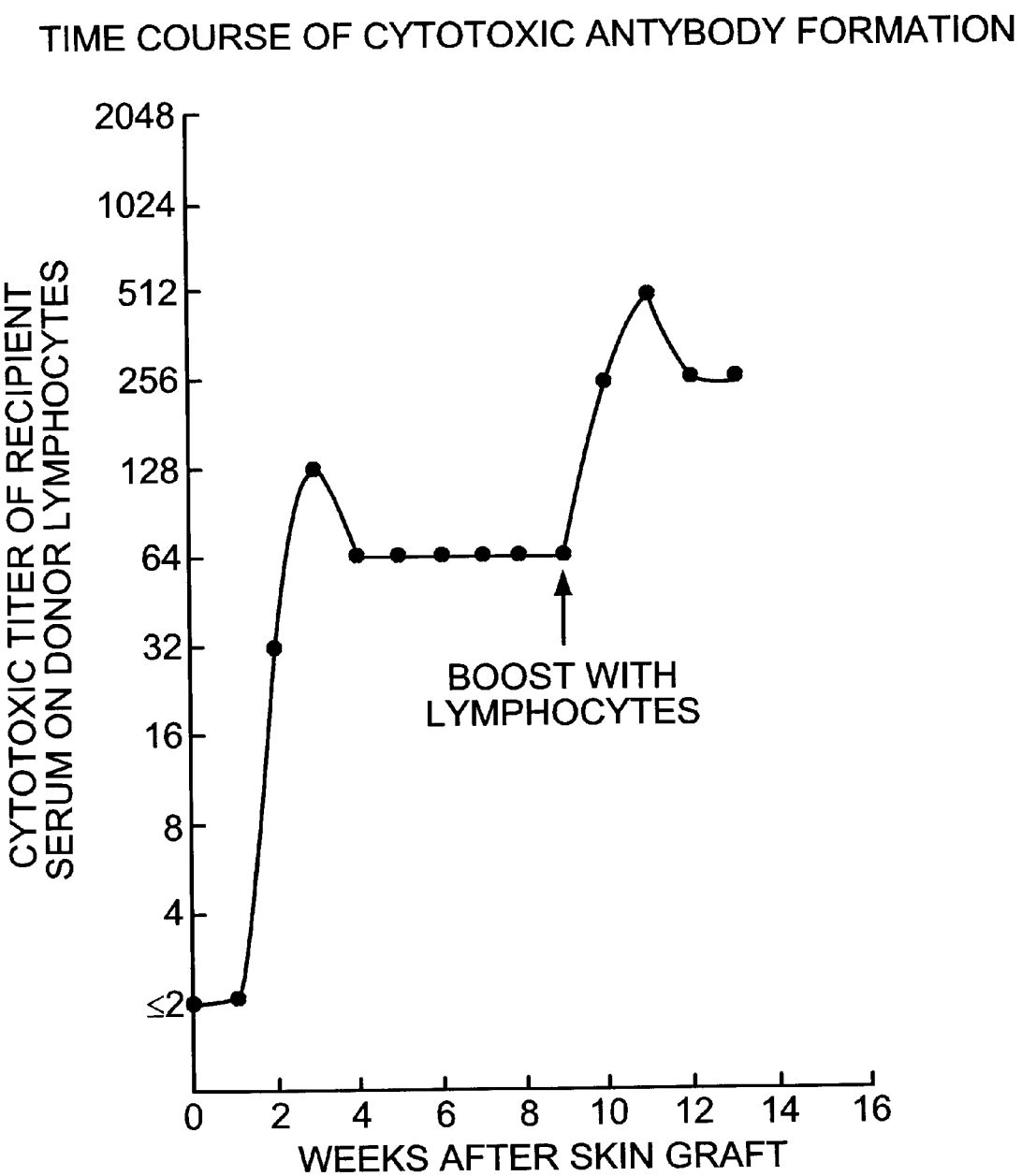
FIG. 1 is a depiction of a time course of cytotoxic antibody formation.

Many important advances in modem transplantation immunology have been made possible by the availability of inbred strains of mice and rats. The production of such strains involves sequential brother-sister mating for more than 20 generations, by which time>98% of segregating loci would be expected to have become fixed, that is, homozygous for one of the four possible alleles that might have been present at the time of the first brother-sister mating. As such, animals of an inbred strain are essentially identical to one another, i.e., are genetically similar to identical twins. From an experimental viewpoint, this removes many of the genetic factors that lead to heterogeneity of experimental results, making it possible to evaluate more accurately the effect of specific treatments on the course of biologic phenomena. In the case of transplantation biology, the availability of such inbred strains made possible the discovery of the laws of transplantation and permitted the identification and characterization of numerous transplantation antigens.

Despite the enormous usefulness of mice for studies of transplantation, there are a variety of areas of research, especially preclinical research, in which large animals have advantages over rodent models. These advantages have practical importance, such as meeting size requirements for some surgical transplantation procedures. They also have theoretical importance in terms of similarity to humans in physiologic and immunologic characteristics. However, true inbreeding would not be feasible for most large animal species within a reasonable period of time, since the minimum time necessary for 20 sequential pedigreed brother-sister matings is approximately 7 years for mice but would range from 30–200 years for the commonest large experimental animals. In addition, during the process of inbreeding many strains are lost due to the fixation of recessive lethal mutations.

For the purposes of transplantation biology, it is clear that the major histocompatibility complex is of overwhelming importance in determining the outcome of transplants. Therefore, the decision was made to produce a large animal model consisting of partially inbred animals homozygous for different alleles at the MHC. For this purpose, a selective pedigreed inbreeding scheme was used in which breeders were selected on the basis of characteristics attributable to the MHC.

Miniature swine, in particular, exhibit several attractive characteristics: 1. Breeding characteristics. Like their domestic counterparts, miniature swine reach sexual maturity at an age of 4–5 months, more preferably 6–7 months. They give birth to multiple offspring (3–10 per litter), making it possible to select appropriate animals at each generation. In addition, they have an estrous cycle every 3 weeks, permitting breeding throughout the year. 2. Similarity to humans. Miniature swine reach an adult size of 200–300 pounds, in contrast to domestic swine that attain weights of over 1000 pounds and are therefore unmanageable as laboratory animals. The size of miniature swine makes it possible to study animals of weights approximately equivalent to that of human beings. Many aspects of the porcine immune system are also very similar to that of human beings, and swine lymphocytes can generally be treated by procedures identical to those optimized for human studies. In addition, swine are physiologically similar to humans and have been an important model for cardiovascular research.

Accordingly, utilizing a selective inbreeding scheme, a herd of partially inbred miniature swine has been developed, in which the MHC equivalent-termed swine leukocyte antigen (SLA) in swine—has been fixed for three alleles. The initial breeders were chosen from different, independently established herds of miniature swine. The initial boar was purchase from Vita Vet Laboratories, Marion, Ind. and the initial sow was a "pigmee pig" purchased from the Hormel Institute, Austin, Tex.

Further breeding of the MHC inbred herds by brother-sister matings within each of the herd was performed as described in Sachs, et al. (1976) *Transplantation* 22: 559–567 the contents of which are incorporated herein by reference, in an attempt to derive true inbred lines.

Transgenic Swine

Swine, cells, tissues, organs and other compositions of the invention can include a transgene.

In preferred embodiments the transgene encodes a xenogeneic, e.g., a human protein, e.g., a class I MHC protein, e.g., an HLA A, B, C or G gene. The inclusion of a xenogeneic class I gene can be used to prolong acceptance of a graft, as is described in U.S. Ser. No. 08/692,843, filed Aug. 2, 1996, and hereby incorporated by reference.

In preferred embodiments the transgene includes an a subunit, e.g., an HLA class I gene, e.g., an HLA C gene.

Where the transgene includes an HLA C gene, the allele, by way of example, can be any Cw1, Cw2, Cw3, Cw4, Cw5, Cw6, Cw7, Cw8, Cw9, Cw7/8v, or Cw10 allele. Alleles of HLA class I genes can often be classed into reactivity groups wherein an allele from a reactivity group can confer protection against NK cells specific to other alleles in the reactivity group. Thus, in preferred embodiments, the transgene includes an allele which is a member of a reactivity group, e.g., a Group 1 allele, e.g., any of an HLA C Cw2, Cw4, Cw5, or Cw6 allele, or a Group 2 allele, e.g., any of an HLA C Cw1, Cw3, Cw7, or Cw8 allele. In other preferred embodiments the allele has: an Asn at residue 77 and a Lys at residue 80; or a Ser at residue 77 and an Asn at residue 80.

In preferred embodiments the transgene includes an HLA A gene. In other preferred embodiments the transgene includes an HLA B gene.

In other preferred embodiments the transgene includes an HLA G gene, e.g., any of alleles I-IV of HLA G.

In preferred embodiments: the transgenic swine cell, tissue or organ, includes, in addition to the first transgene, a second transgene which includes a class I MHC protein. In preferred embodiments the second transgene includes an HLA class I gene, e.g., an HLA A, B, C or G gene. In preferred embodiments the first transgene includes an allele from a first reactivity group and the second transgene includes an allele from a second reactivity group. For example, the first transgene includes a Group I allele, e.g., any of an HLA C Cw2, Cw4, Cw5, or Cw6 allele, and the second transgene includes a Group 2 allele, e.g., any of an HLA C Cw1, Cw3, Cw7, or Cw8 allele. In preferred embodiments the first transgene encodes an allele which has an Asn at residue 77 and a Lys at residue 80 and the second transgene encodes an allele which has a Ser at residue 77 and an Asn at residue 80. In other preferred embodiments the second transgene encodes a human β subunit, e.g., a β-2 microglobulin gene.

In preferred embodiments the transgene includes a chimeric class I gene, e.g., a chimeric HLA A, B, C, or G gene. The chimeric transgene can include a first portion derived from a first allele of a gene encoding a class I protein and a second portion derived from a second allele of the gene encoding the class I protein. In other embodiments, the class I gene is a synthetic sequence selected for the ability to produce a protein which protects a target cell from attack from more than one class of NK cells. In preferred embodiments the transgene includes a gene, e.g., a chimeric or mutated HLA C gene, which confers protection to more than one class of NK cells, e.g., an allele of HLA C having serine at position 77 and lysine at position 80, see e.g., Biassoni, 1995, *J. Exp. Med. Vol.* 182: 605–609, hereby incorporated by reference. See also Moretta et al., 1996, *Ann. Rev. Immunol.* 14: 619–648, hereby incorporated by reference, which together with the disclosure herein, provides guidance for altering critical residues in the HLA C genes.

In yet other preferred embodiments the transgenic swine cell, tissue or organ, includes one or more, or all of, of a transgene which encodes an HLA A gene, a transgene which encodes an BLA B gene, a transgene which encodes an HLA C gene, and a transgene which encodes an HLA G gene.

Swine, cells, tissues, organs and other components of the invention can include a transgene which encodes a graft-supporting protein, e.g., a human growth factor or cytokine receptor, e.g., a growth factor or cytokine receptor involved in the regulation of hematopoiesis. Examples of growth factor or cytokine receptor include the receptors for G-CSF, SCF, GM-CSF, IL-3, IL-6, IL-11, IL-2, Epo, and uteroferrin.

In other preferred embodiments the transgene encodes a graft-supporting protein, e.g., a human adhesion molecule, e.g., an adhesion molecule involved in engraftment and/or maintenance of hematopoietic cells. Examples of human adhesion molecules include VLA-4, c-kit, LFA-1, CD11a, Mac-1, CR3, CD11b, p150, p95, CD11c, CD49a, LPAM-1, CD49d, CD44, CD38, and CD34.

In yet other preferred embodiments the transgene encodes a recipient or donor protein, e.g., a cytokine, which directly, or indirectly (e.g., by the stimulation or inhibition of the level of activity of a second cytokine), inhibits an immune response mounted by donor cells against the recipient, e.g., IL-10, IL-4, IL-2, or TGF-β.

In yet other preferred embodiments the transgene encodes a chimeric molecule, e.g., a chimeric lymphokine, e.g., PIXY123.

In yet other preferred embodiments the transgene encodes a graft-supporting protein, e.g., a recipient or donor cytokine, which directly, or indirectly (e.g., by the stimulation or inhibition of the level of activity of a second cytokine), inhibits an immune response mounted by recipient cells against donor tissue, e.g., IL-10, IL-4, IL-2, or TGF-β.

In yet other preferred embodiments the transgene inhibits the expression or action of a gene product which is graft-antagonistic, e.g., by decreasing the expression of the gene product. For example, the transgene is a mutationally inactivated copy of a gene which encodes a donor graft-antagonistic protein, e.g., the donor cells' B-7 receptor, CD27 receptor, or LFA-3 receptor, or a donor receptor for a host cytokine, and which when inserted into the donor genome, e.g., by homologous recombination, results in an endogenous gene which is misexpressed or which is mutationally inactivated, by, e.g., the introduction of a mutation, e.g., a deletion, into an endogenous genomic copy of the gene which encodes the donor cells' B-7 receptor, CD27 receptor, or LFA-3 receptor, or a donor receptor for a host cytokine.

The transgene can be one which encodes an anti-sense RNA which, directly or indirectly, inhibits the expression or action of a recipient-derived graft-antagonistic protein, e.g., an anti-sense RNA which inhibits the expression of a donor-encoded B-7 receptor, CD27 receptor, or LFA-3 receptor, or a donor receptor for a host cytokine.

The transgene can be one which encodes a dominant negative mutation in a gene product which is graft-antagonistic, e.g., a donor cell receptor for a host cytokine or donor B-7 receptor, CD27 receptor, or LFA-3 receptor.

In yet other preferred embodiments the transgene includes a nucleic acid encoding a human peptide, e.g., a hematopoietic peptide, operably linked to: a promoter other than the one it naturally occurs with; a swine promoter, e.g., a swine hematopoietic gene promoter; a viral promoter; or an inducible or developmentally regulated promoter.

EXAMPLES

Materials and Methods

Animals. In order to assure diversity of the MHC at the outset (since at least two different MSLA homozygous herds were desired), the initial breeds were chosen from different independently established herds of minipigs. The initial boar, pig 1, was purchased from Vita Vet Laboratories, Marion, Ind., and the initials sow, pig 2, was a "pigmee pig" purchased from the Hormel Institute, Austin, Minn. The animals were housed indoors in 10-×14-foot pens on concrete floors and were fed on Purina complete sow chow. Pregnant sows were moved into separate box stalls for farrowing.

Immunization. Initial typing antisera were obtained by full thickness skin grafting between pigs 1 and 2, prior to breeding. The animals were anesthetized with ketamine and halothane and a 3-inch square, full thickness skin graft was transferred reciprocally between their posterior thoraces. Serum samples were drawn prior to grafting and at weekly intervals thereafter.

Booster injections with approximately 108 live peripheral lymphocytes were performed after cytotoxic titers had plateaued following skin graft rejection. Lymphocytes were obtained from approximately 50 ml of heparinized donor blood by the Ficoll-Hypaque sedimentation method of Boyum (described in Boyum A. (1968) *Scand. J. Clin. Lab. Invest.* 21:97). These were injected intramuscularly into the recipient animal and serum was obtained at weekly intervals thereafter.

Small blood samples (up to 10 ml) were obtained by venipuncture of ear veins. Larger samples were obtained by venipuncture of the anterior vena cava with the animal in a supine position.

Technique-for Skin Grafting

Split-thickness skin grafts (STSG) measuring approximately 0.4 mm×6.0 cm×4.0 cm were taken from the dorsal surface of the ear and placed on a full-thickness graft bed on the posterior thorax. Each minipig received an autograft and an allograft, held in place by a compression dressing of Vaseline gauze. Dressings were removed on the third day, and grafts were inspected daily until rejection was complete. Serum was obtained from each minipig prior to grafting and at regular intervals thereafter; all sera from a skin allograft recipient were tested against donor lymphocytes in the two-stage cytotoxic assay.

Serology Hemagglutination assays were performed in a crossmatch fashion, adding a few µl of washed packed red cells to a drop of fresh plasma, incubating at 37° C. for 10 minutes, and scoring agglutination from $1^+$ to $4^+$ under low power light microscopy.

Trypan blue cytotoxicity tests were performed in disposable U-bottom Microtiter plates (Cooke Engineering Co., Alexandria, Va.) using lymphoid cell suspensions obtained by Ficoll-Hypague sedimentation of fresh heparinized and passage through loosely packed washed glass wool. A two-stage cytotoxic assay using rabbit complement was performed as previously (described in Sachs D. H. et al. (1971) *J. Immunol.* 107: 481).

In vitro absorptions of antisera were performed by mixing appropriate number of lymphoid cells with antiserum in a 15-ml conical centrifuge tube. The cells and serum were mixed and incubated at 4° C. for 0.5 hour, with mixing at 15 minutes, and the tube was then centrifuged at 900 g for 15 minutes to yield an absorbed antiserum.

Mixed lymphocyte cultures. Lymphocyte separations were prepared as above, except that a sterile technique was used for the venipuncture and throughout the preparation of the lymphocyte suspension. Tissue culture medium consisted of RPMI 1640 with 100 units of penicillin per ml, 100 µg of streptomycin per ml, and 5% fetal pig serum.

For one-way MLC reactions, one-half of each cell suspension was either irradiated with 2,000 R from a "Gammator M" cesium source (Isomedix Inc., Parsippany, N.J.) or was incubated at 37° C. for 30 minutes with 25 µg of mitomycin C (Nutritional Biochemical Co., Cleveland, Ohio) per $5 \times 10^6$ cells and was washed 5 times with medium. Cell suspensions were adjusted to $5 \times 10^6$ cells/ml and 0.1 -ml aliquots of each cell suspension was mixed in the wells of V-bottom Microtiter plates (Cooke Engineering Co.). Controls consisted of 0.1 ml of treated responder cells from the same animal. All test combinations were run in triplicate. Plates were incubated in 100% humidity at 37° C. with 5% CO2 in air in a National incubator. Each well was pulsed with 1 µCi of tritiated thymidine (Amersham/Searle Corp., Arlington Heights, Ill.) for 4 hours on the 5th day, and cultures were then harvested with a MASH II (Microbiological Associates, Bethseda, Md.) harvester. Liquid scintillation counting was performed in Yorktown Hydromix solution. Results were expressed as ratios of experimental cpm versus control cpm. The control for one-way MLCs was the activity incorporated in autologous cultures described above. The control values for two-way MLCs were taken as the sum of one-half of the incorporation of each of the control cultures for the two cells tested.

Example 1

Production of Homozygous Miniature Swine Leukocyte Antigen (MSLA) Herds

Serology. Natural anti-red cell antibodies were found to be present in several combinations of pigs that were tested. Unlike the situation in man, these red cell antibodies appeared to be cytotoxic to lymphocytes under the conditions of the cytotoxic assay. Table 1 shows a typical example of the results obtained with preimmune serum in such a combination.

TABLE 1

Lymphocytotoxicity of natural antibodies

| Immunization status of serum donor | Absorption with target strain red cells | Aggiutination of target strain red cells | Medium control | Complement control | Lymphocytotoxicity on target strain lymphocytes Antiserum dilution | | | | | | | | |
|---|---|---|---|---|---|---|---|---|---|---|---|---|---|
| | | | | | 1 | 2 | 4 | 8 | 16 | 32 | 64 | 128 | 256 |
| Pre immune | − | +2 | <10 | <10 | 70 | 71 | 55 | 22 | <10 | <10 | <10 | <10 | <10 |
| | + | 0 | <10 | <10 | <10 | <10 | <10 | <10 | <10 | <10 | <10 | <10 | <10 |
| Pre immune | − | +2 | <10 | <10 | >80 | >80 | >80 | >80 | >80 | >80 | 74 | 22 | <10 |
| | + | 0 | <10 | <10 | >80 | >80 | >80 | >80 | >80 | >80 | 51 | 13 | <10 |

As indicated, when the hemagglutination was positive on red cells, a low titer of cytotoxic antibody was also seen in the preimmune serum. Absorption of such sera with five parts of packed washed red cells was found to remove both the hemagglutinating antibodies and the cytotoxic activity. Cytotoxic titers of postimmune antisera (also indicated in Table 1) were not altered by a similar red cell absorption, indicating that the converse was not true, i.e., anti-MSLA antibodies are not absorbed significantly by pig red cells.

Unlike many mammalian species for which normal rabbit serum frequently contains large amounts of natural cytotoxic antibodies, satisfactory rabbit complement was readily obtained for miniature swine lymphocytes. Serum from each of four outbred New Zealand rabbits tested produced less than 10% background cytotoxicity at a 1:2 dilution of complement and provided adequate complement to give complete cytotoxic lysis of sensitized target cells to a dilution of greater than 1:8. This makes it easy to work in relative complement excess for this species. In addition, miniature swine lymphocyte preparations obtained by Ficoll-Hypaque separation of peripheral blood were found to be very satisfactory target cells for cytotoxic assays. These cells hi remained viable in the medium used for cytotoxic assays (Medium 199 containing 0.1% gelatin) for at least 2 days at 4° C.

Course of cytotoxic antibody production. Animals that received skin grafts for immunization showed rejection by visual inspection between 8 and 10 days. Cytotoxic antibodies appeared in the host serum by 2 weeks after grafting and remained elevated for several weeks thereafter. Following a boost with peripheral lymphocytes, the titer of cytotoxic antibodies generally rose by several 2-fold dilutions and then again plateaued. A typical pattern of the course of cytotoxic antibodies following skin grafting and boosting in these miniature swine is shown in FIG. 1. Recipient pig's serum was tested for cytotoxicity against donor lymphocytes each week after grafting, using the standard microcytotoxicity assay as described in Sachs, et al. (1976) *Transplantation* 22: 559–567. Cytotoxic titers were taken as the last dilution of sera producing more than 50% lysis of target cells.

Figure 2:
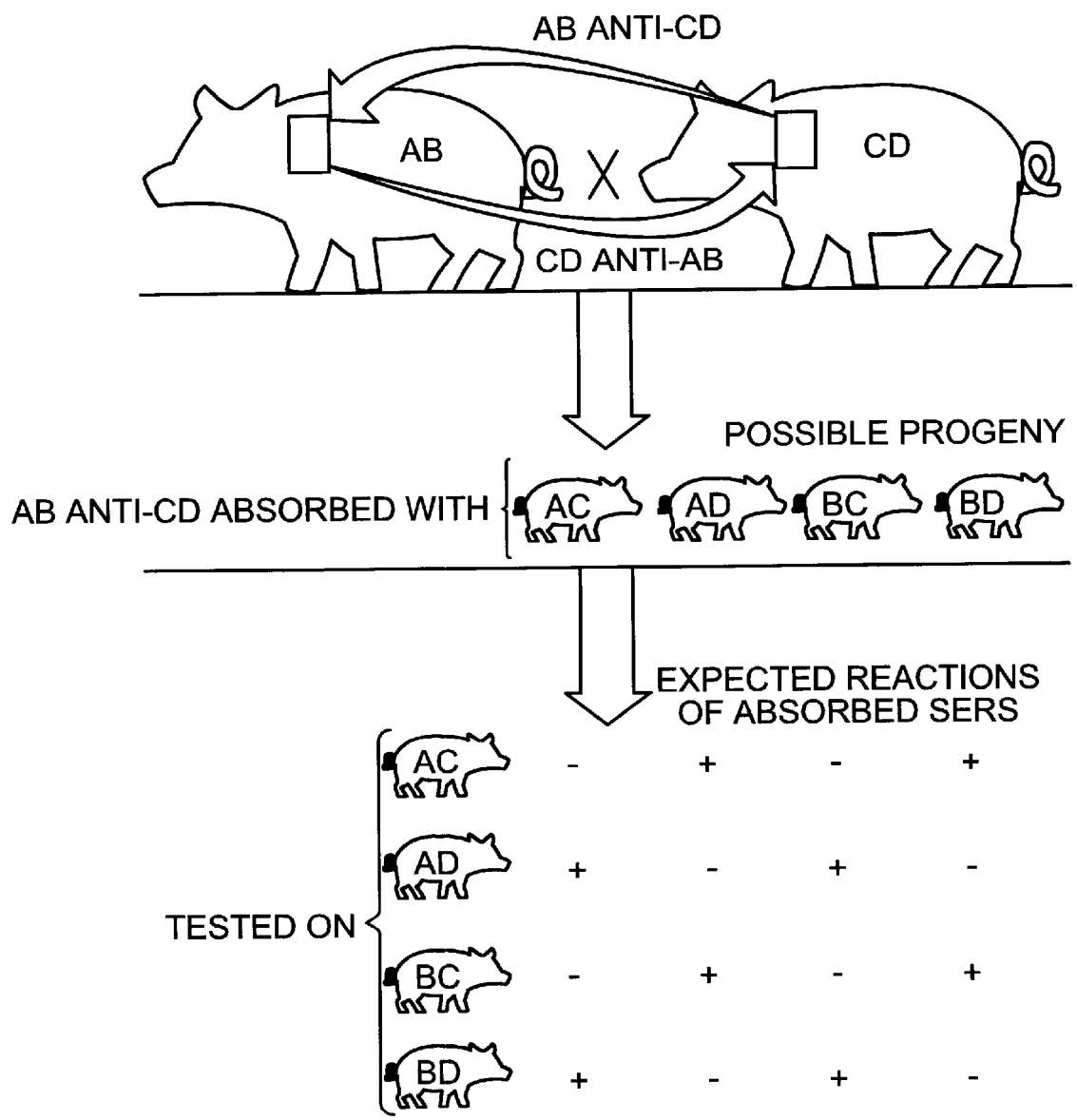
FIG. 2 is a schematic representation of the serological analysis of the first generation progeny. An analysis of the progeny for MHC genotypes by absorption of cytotoxic antisera is shown schematically for the case of maximum possible heterogeneity. Experimental details are provided in Sachs, et al. (1976) *Transplantation* 22: 559–567.

Serological analysis of first generation offspring. In a wide variety of mammalian species that have been studies so far, rejection of allografts is accompanied by the appearance in the recipient's serum of antibodies detecting products of the MHC antigens of the donor. Assuming that there is one MHC in miniature swine and that the initial animals chosen for breeding differed in alleles at this locus, we can assign letters for the genotypes at the MHC of each of the pigs arbitrarily as AB for pig 1 and CD for pig 2. This represents the maximum heterogeneity that would be possible for a single autosomal locus. The offspring of pig 1 and pig 2 would thus be of 4 possible genotypes, as indicated schematically in FIG. 2.

If the immunization of pig 1 (AB) with tissue from pig 2 (CD) produced antibodies detecting both alleles at the MHC, we could expect the antibodies to consist of anti-C and anti-D components. Similarly, pig 2 (CD) immunized with pig 1 (AB) should produce anti-A and anti-B antibodies. It should thus be possible by absorption studies to determine which of the offspring inherited each of the theoretically possible alleles, as shown schematically in FIG. 2 for one of the sera. Serum 308 (pig 1, anti-pig 2) and serum 309 (pig 2, anti-pig 1) were tested by such an absorption analysis on each of the offspring that they produced. The results with serum 308 tested on four of the offspring (assigned identification numbers 5, 6, 8, and 9) that were subsequently chosen for further breeding are shown in Table 2.

TABLE 2

Absorption pattern of antiserum 308 (pig 1 anti-pig 2) in pigs of the first generation

| Test cells | Complement control | Lysis after absorption with | | | | |
|---|---|---|---|---|---|---|
| | | None | 5 | 6 | 8 | 9 |
| 5 | <10 | >80 | 47 | 57 | >80 | >80 |
| 6 | <10 | >80 | 16 | <10 | >80 | >80 |
| 8 | <10 | >80 | >80 | >80 | 60 | 47 |
| 9 | <10 | >80 | >80 | >80 | 52 | 56 |

Despite the incompleteness of the absorptions, it was clear from these results that the four offspring could be separated into two groups, each having received one of the possible MSLA alleles from parent 2. Pigs 5 and 6 were therefore arbitrarily assigned MSLA haplotype C and pigs 8 and 9 were assigned the haplotype D.

However, when a similar absorption study was carried out with serum 309, all of the offspring of this mating were found capable of absorbing cytotoxic reactivity against all of their siblings, as indicated in Table 3.

TABLE 3

Absorption pattern of antiserum 309 (pig 2 anti-pig 1) in pigs of the first generation

| Test cells | Complement control | Lysis after absorption with | | | | |
|---|---|---|---|---|---|---|
| | | None | 5 | 6 | 8 | 9 |
| 5 | <10 | >80 | 23 | 25 | 23 | 37 |
| 6 | <10 | >80 | <10 | <10 | <10 | <10 |
| 8 | <10 | >80 | <10 | <10 | 17 | 16 |
| 9 | <10 | >80 | 11 | <10 | 16 | 13 |

Repeated absorptions with increasing numbers of lymphocytes showed the same pattern of mutual reactivity of all the siblings. It therefore appeared that only one haplotype was transmitted from pig 1 to all of the offspring in this mating and only one haplotype designation, A, could be assigned to all of these offspring. It seems possible either than pig 1 was in fact a homozygote at the MHC (i.e., AA) or that he was a heterozygote (AB) but that only the A allele was transmitted to his offspring. The latter possibility could have been due to chance alone (P=0.06) or because of unknown selective pressures. As indicated below, all of the subsequent typing data obtained, confirmed the transmission of only a single MSLA haplotype from pig 1.

Serological typing of subsequent generations. Only three possible MSLA genotypes would be expected from the breeding of two identical heterozygotes (i.e., AC×AC–AA+2AC+CC). In addition, antisera 308 and 309 should be essentially monospecific with respect to their reactions with such offspring. Therefore, no absorptions of these sera were required in order to determine which allele each had inherited. A typical example of the genotyping of one litter obtained from pigs 5 and 6 is indicated in Table 4.

TABLE 4

Typing of the second generation

| Parents | Offspring | Complement control | Maximum % lysis by: | | Assignment |
|---|---|---|---|---|---|
| | | | Serum 308 (pig 1, anti-pig 2, anti-AA-CD) | Serum 309 (pig 2, anti-pig 1, DC anti-AA) | |
| Pig 5 (AC) x Pig 6 (AC) | 42(M) | <10 | >80 | <10 | CC |
| | 43(F) | <10 | <10 | >80 | AA |
| | 44(M) | <10 | >80 | >80 | AC |
| | 45(F) | <10 | >80 | >80 | AC |
| | 46(F) | <10 | >80 | <10 | CC |
| | 47(M) | <10 | >80 | >80 | AC |
| | 48(F) | <10 | >80 | >80 | AC |
| | 49(F) | <10 | >80 | <10 | CC |
| | 50(F) | <10 | >80 | >80 | AC |
| Pig 8 (AD) x Pig 6 (AD) | 23 (M) | <10 | >80 | <10 | DD |
| | 24(M) | <10 | >80 | <10 | DD |
| | 25(F) | <10 | >80 | <10 | DD |

Figure 3:
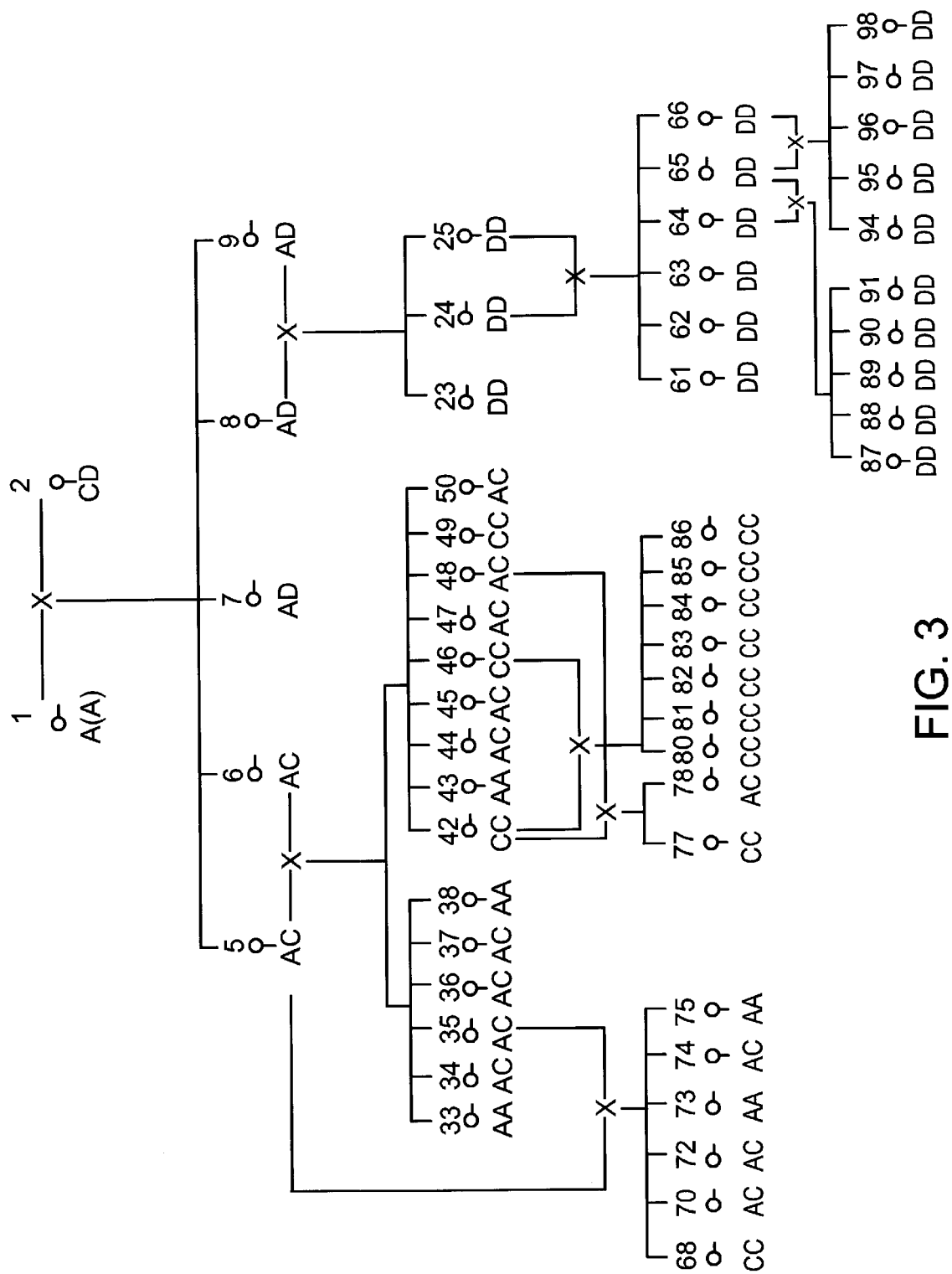
FIG. 3 is a schematic representation of the breeding scheme employed in the production of MSLA homozygous miniature swine.

Similar serological typing was carried out for all of the offspring obtained from these breedings. FIG. 3 presents a summary of the genotype assignments of the miniature swine that have thus far been obtained from the original pigs 1 and 2. It is apparent from this figure that, by the third generation, approximate breeders had been obtained to produce three herds of miniature swine, each homozygous for a different set of MSLA genes.

MLC typing. In other mammalian species so far studied, including man, mouse, rat guinea pig, dog, and domestic swine, mixed lymphocyte culture (MLC) stimulation has correlated with serological typing for the MHC. It therefore seemed probable that if the MHC was indeed being typed for serologically, MLC reactions should corroborate the genotyping. MLC typing of the earlier generations of these miniature swine was carried out under suboptimal conditions, using 5% fetal calf serum rather than fetal pig serum. Stimulation levels were low, but nevertheless significant and reproducible. After introduction of fetal pig serum into the medium, stimulations rose from 2-fold to as high as 10- to 20-fold. In all cases there was concordance between MLC reactivity ad the expected genotype at the MHC obtained by serological cytotoxicity typing. Table 5 shows the MLC data obtained for the first generation offspring of pigs 1 and 2.

TABLE 5

MCL reactions of first generation offspring

| Cells cultured | Control cpm (½A + ½B) | Experimental | Stimulation ratio (experimental/control) |
|---|---|---|---|
| 5(AC) + 6(AC) | 2,757 ± 546 | 2,966 ± 1,079 | 1.08 |
| 5(AC) + 8(AD) | 5,795 ± 1,177 | 13,287 ± 1,013 | 2.29 |
| 5(AC) + 9(AD) | 6,116 ± 1,453 | 11,811 ± 3,465 | 1.93 |
| 6(AC) + 8(AD) | 4,464 ± 931 | 10,151 ± 1,434 | 2.28 |
| 6(AC) + 9(AD) | 4,785 ± 1,207 | 11,216 ± 449 | 2.35 |
| 8(AD) + 9(AD) | 7,723 ± 1,838 | 7,401 ± 1,723 | 0.96 |

Despite the low stimulation values obtained, it is clear from these data that the same assignment of genotypes as was made on the basis of the cytotoxicity typing can account for the patterns of MLC stimulation seen. Table 6 shows a more recent analysis of MLC reactions between several animals homozygous for CC by serological analysis of MSLA genotypes (see FIG. 3).

TABLE 6

MLC reactions of serological homozygotes

| Cells cultured | Control | Experimental cpm | Stimulation ratio |
|---|---|---|---|
| 42(CC) + 66(DD) | 1,593 ± 319 | 23,372 ± 2,607 | 14.67 |
| 46(CC) + 66(DD) | 2,677 ± 809 | 10,090 ± 458 | 3.77 |
| 68(CC) + 66(DD) | 1,025 ± 180 | 11,658 ± 1,379 | 11.37 |
| 77(CC) + 66(DD) | 1,151 ± 74 | 4,921 ± 353 | 4.28 |
| 42(CC) + 46(CC) | 2,899 ± 564 | 3,709 ± 654 | 1.28 |
| 42(CC) + 68(CC) | 2,113 ± 231 | 2,055 ± 492 | 0.97 |
| 42(CC) + 77(CC) | 2,147 ± 287 | 1,610 ± 304 | 0.75 |
| 46(CC) + 68(CC) | 1,891 ± 476 | 2,337 ± 434 | 1.24 |
| 46(CC) + 77(CC) | 1,922 ± 532 | 1,466 ± 159 | 0.76 |
| 68(CC) + 77(CC) | 1,139 ± 198 | 1,374 ± 229 | 1.20 |

Since the animals were taken from different subships, this type of analysis provides a stringent test for the absence of other genetic factors causing MLC reactivity not associated with the MHC. As can be seen from these data, no significant stimulation was obtained in two-way MLC reactions between the MSLA homozygous identical animals. Also shown in the table are one-way control MLC reactions in which each of the CC homozygotes were found to be capable of mounting a significant response to DD cells, indicating that the nonresponsiveness seen in the two-way cultures was not due to inability of any of the CC cells to proliferate. In addition, a variety of one-way MLC reactions were performed between homozygous and heterozygous animals sharing one MSLA haplotype (e.g., AA+ACx and AC+AAx). In such experiments significant stimulation ratios were obtained only in the direction of AA+ACx. Thus the data are entirely consistent with the presence of a strong MLC stimulatory locus (or loci) within or closely linked to the serologically defined MSLA locus.

Example 2

Production of Miniature Swine Homozygous at MHC (Haplotype D) and 85% Homozygous at all Other Genetic Loci In this example, miniature swine homozygous for the MSLA haplotype D were first mated in a strictly non-brother-sister fashion for 20–25 generations and then strictly brother-sister mated for 7 generations in order to obtain a herd of animals homozygous at other genetic loci. Split-thickness skin grafts were used to quantitate the percentage of inbreeding. By the seventh generation, animals approximately 85% homozygous at all other genetic loci were obtained.

Example 3

Cocultivation of Miniswine Peripheral Blood Mononuclear Cells with Human 293 Cells and Porcine St Iowa Cells Objective The purpose of this study was to cocultivate mini swine peripheral blood mononuclear cells, (PBMCs) with the porcine endogenous retrovirus (PERV) susceptible human cell line 293 (ATCC CRL-1572) and with the porcine susceptible cell line ST Iowa (ATCC CRL-1746).

Rationale

A safety consideration in xenotransplantation procedures is the possible transmission of a zoonotic infectious agent from donor to recipient. Recent publications have described the detection of endogenous retroviral sequences in pigs, a source of cells and organs in xenotransplantations. Additionally some continuous porcine cell lines, which contain similar retroviral sequences, produce PERV which is infectious to other cell types, including human 293 cells. Consequently, it is prudent to assess the infectivity, if any, of PERV related sequences present within the genomes of porcine cells which are to be used in xenotransplantation.

Experimental Design

A. Study Overview

Isolated pig peripheral blood mononuclear cells (PBMCs) were activated for 3 days with phytohemaggluttinin (PHA), phorbol myristate acetate (PMA), and IL-2. Subsequent to activation, PBMCs, both irradiated and non-irradiated, were cocultivated with the cell lines 293 (a transformed human embryonic kidney cell line) and ST Iowa (a continuous porcine testis cell line).

The cocultivation lasted for approximately 35 days. Cultures were passaged when they were 90 to 100% confluent, (but not prior to day 6). On approximately days 6, 21, and 35, cell free supernatants were harvested from all cultures. This timeline was subject to the condition that supernatants cannot be harvested until 2 days post passaging of the culture.

Harvested cell free supernatants from days 6, 21, and 35 were analyzed by RT-PCR for porcine endogenous retrovirus (PERV). Enzymatic RT assays were performed on day 35 cell free supernatants.

On approximately day 21, approximately five fold concentrated cell free supernatants from some cultures were inoculated onto polybrened, subconfluent 293 monocultures. Blind passaged cultures included PBMC monocultures, PBMC and irradiated PBMC/293 cocultures, PBMC and irradiated PBMC with ST Iowa, the 293, ST Iowa and PK-15 (ATCC CCL-33) monocultures and the irradiated PK-15/293 coculture. These blind passage cultures were maintained for 21 days and passaged when necessary. At day 21, RT-PCR for PERV was performed on cell free supernatants and DNA PCR for PERV was performed on cells.

Cells were harvested from each of the surviving cultures in the study on the last day of the study, and DNA was extracted from cells. DNAs were amplified with pig specific multicopy gene primers to determine if porcine cells were present in the cocultivations.

B. Specific Procedures

1. Initiation of Monocultures and Cocultures a. Activation of PBMCs

PBMCs from mini swine blood were isolated by Ficoll density gradient separation. Washed buffy coat cells were counted and aliquoted into T25 flasks. Five ml of 1×10⁶ PBMCs/ml were placed in each flask. Medium consisted of RPMI 1640, 15% irradiated FBS, L-glutamine, antibiotics, IL-2, PHA and PMA. Cells were incubated at 7–10% CO2, at 37° C. PBMCs remained in this medium for 3 days.

b. Seeding Procedures

After 3 days aliquots of cells were tested for thyrnidine uptake. The activated cells were plated into P 100 tissue culture dishes and allowed to sit for 4–6 hours to remove adherent cells. Aliquots of approximately 5×10⁶ viable non-adherent PBMCs were pelleted by centrifuging at a setting of 800 rpm for 8 minutes at room temperature. Each aliquot of pelleted cells was resuspended in 5 ml of medium consisting of heat inactivated DMEM with 10% FBS, L-glutamine, antibiotics, and IL-2.

Aliquots of 5 ml of cell suspension, each containing 5×10⁶ PBMCs, were seeded as follows:

(1) One aliquot was placed into each of four T25 flasks. Two flasks were X-irradiated for the appropriate period of time (approximately 2000 rads). Two flasks remained unirradiated.

(2i) $1.0 \times 10^6$ 293 cells were placed into each of 2 sterile 15 ml centrifuge tubes. The cells were pelleted by centrifugation and the supernatants discarded. Each of two pellets of 293 cells were resuspended in an aliquot of 5 ml of $5 \times 10^6$ PBMCs. After gentle mixing, one cocultivation was placed into each of two T25 flasks.

(2ii) $1.0 \times 10^6$ 293 cells were placed into each of 2 sterile 15 ml centrifuge tubes. The cells were pelleted by centrifugation and the supernatants discarded, Each of two pellets of 293 cells were resuspended in an aliquot of 5 ml of $5 \times 10^6$ irradiated PBMCs (approximately 2000 rads).: After gentle mixing, one cocultivation was placed into each of two T25 flasks.

(2iii) $0.5 \times 10^6$ ST Iowa cells were placed into each of 2 sterile 15 ml centrifuge tubes. The cells were pelleted by centrifugation and the supernatants discarded. Each of two pellets of ST Iowa cells was resuspended in an aliquot of 5 ml of $5 \times 10^6$ PBMCs. After gentle mixing, one cocultivation was placed into each of two T25 flasks.

(2iv) $0.5 \times 10^6$ ST Iowa cells was placed into each of 2 sterile 15 ml centrifuge tubes. The cells were pelleted by centrifugation and the supernatants discarded. Each of two pellets of ST Iowa cells was resuspended in an aliquot of 5 ml of $5 \times 10^6$ irradiated PBMCs (approximately 2000 rads). After gentle mixing, one cocultivation was placed into each of two T25 flasks.

c. The positive control cultures were as follows
Duplicate flasks of PK-15 cells seeded the preceding day at $1 \times 10^6$ cells per flask were X-irradiated (approximately 2000–10,000 rads). Following irradiation, $1.0 \times 10^6$ 293 cells per flask were overlaid on the PK-15 cells. Duplicate flasks of unirradiated PK-15 cells seeded at $0.5 \times 10^6$ cells/flask.

d. The negative control cultures were as follows
Duplicate cultures of unirradiated 293 cells seeded at $1.0 \times 10^6$ cells/flask. Duplicate cultures of unirradiated ST Iowa cells seeded at $0.5 \times 10^6$ cells/flask.

All cultures were maintained without passaging for 6 days post initiation of cocultures. Six days post initiation of cocultures, all cultures that were 90% or more confluent were passaged using a split ratio appropriate to the cell type. PBMC cultures were considered 100% confluent when the cell density reached $2 \times 10^6$ cells/ml. Cultures which are less than 90% confluent were refed as necessary until they were 90–100% confluent, at which time they were passaged. 293 and ST Iowa monocultures, 293/PBMC cocultures, and ST Iowa/PBMC cocultures were split a total of 5 times prior to day 34 post irradiation.

After day 6 cultures were maintained in complete 293 medium (DMEM, 10% heat inactivated FBS, 2–4 mM L-glutamine and 1% antibiotics) at 36° C. and 10% CO2 for the duration of the study.

e. $1.0 \times 10^6$ 293 cells were inoculated with approximately 5 fold concentrated cell free supernatants from day 21 harvests. These cultures were maintained and split as necessary for 21 days. Cell free-supernatants and cellular DNA were harvested from these blind passage cultures on day 21. See Table 7.

TABLE 7

| Treatment | Irradiation | Number of Cells in Flask ($\times 10^{-6}$) | Number of Flasks |
|---|---|---|---|
| ST Iowa | No | 0.5 | 2 |
| 293 | No | 1.0 | 2 |
| PBMC | No | 5 | 2 |
| PBMC | Yes | 5 | 2 |
| PBMC | No | 5 | 2 |
| ST Iowa | No | 0.5 | |
| PBMC | No | 5 | 2 |
| ST Iowa | No | 0.5 | |
| PBMC | Yes | 5 | 2 |
| 293 | No | 1.0 | |
| PBMC | No | 5 | 2 |
| 293 | No | 1.0 | |
| PK-15 | Yes | 1 | 2 |
| 293 | No | 1 | |
| PK-15 | NO | 0.5 | 2 |

2. Cell Harvesting and DNA Extraction

Cell viabilities were performed on all monocultures and cocultures on the last day of the cocultivation and the last day of the blind passage. Cultures were then centrifuged, or trypsinized and centrifuged, to pellet cells. To the cell pellets from each of the nine treatments, a 1×lysis buffer was added. Samples were incubated at 56° C. +/−2° C. for 30 minutes and 1–2 hours at 37° C. Lysed samples were phenol/chloroform extracted and precipitated in NaCl and ethanol at −16° C. or below or at −70° C. to −80° C. Samples were centrifuged at a setting of 4° C. The pellets were rinsed with 70–75% ethanol, and centrifuged again at a setting of 4° C. The pellets were air dried.

DNA pellets were dissolved in sterile Tris EDTA (TE) so that DNA equivalent to approximately $1 \times 10^5$ cells (approximately 800 ng of DNA) existed in each 10 (1 sample. Samples were frozen at −70° C. or below until use.

3. Harvesting of Cell Free Supernatants

At all time points, cell free culture supernatants were harvested in the following manner: supernatant was harvested, centrifuged at a setting of 800 rpm for 10–15 minutes, transferred to new tubes and then centrifuged at 2000×g for 15 minutes, filtered through a 0.45 (m cellulose acetate filter, aliquoted and frozen at −70° C. until assayed, if not assayed immediately.

Detection of Porcine Endogenous Retroviruses in Cell Culture Supernatants Using Reverse Transcription and Polymerase Chain Reaction Objective The purpose of this study was to detect RNA sequences specific to the protease region of porcine endogenous retroviruses (PERV) that may exist in pig cells, tissues or organs (Test article).

Rationale

A safety consideration in xenotransplantation procedures is the possible transmission of a zoonotic infectious agent from donor to recipient. Recent publications have described the detection of endogenous retroviral sequences in pigs, a source of cells and organs in xenotransplantations. Additionally some continuous porcine cell lines, which contain similar retroviral sequences, produce PERV which is infectious to other cell types, including human 293 cells.

A sensitive and rapid method for detection of viral RNA and/or RNA transcripts from. proviral retroviruses is RT-PCR. This protocol describes the methods used when testing cell culture fluids for PERV specific RNA sequences.

Experimental Design
A. Sample Preparation

An aliquot of each test article was spiked with positive control RNA prior to extraction in order to show recovery of PERV RNA. In the case of samples from co-cultivation studies, only supernatants from "indicator" cultures test were spiked.

RNA preparation was performed by pipetting supernatants vigorously in the presence of guanidine isothiocyanate and phenol. Chloroform was added and the sample mixed. Samples were then centrifuged. The aqueous phase was transferred to a new tube and isopropanol added. Samples were incubated for approximately 10 minutes at room temperature and then centrifuged. RNA pellets were washed once with 75% ethanol and centrifuged again. RNA pellets were partially air dried before being resuspended.

The pellets were dissolved in DNAse free water or buffer. A DNAse reaction buffer and RNAse free DNAse were added to the sample. Samples were incubated for the appropriate period of time at 37° C. +/-2° C. Subsequent to incubation, the samples were briefly heated to 95° C. +/-2° C. The samples were then be assayed immediately or frozen at -60° C. or below until use.

B. Preparation of Polymerase Chain Reaction Solution

Polymerase chain reaction (PCR~mixtures (master mix) were prepared in the PCR master mix room. Only preparations of master mix occur in this room. Master mix was comprised of sterile molecular biology grade water, reaction buffer, the nucleotides dCTP, dATP, dGTP and dUTP and the enzyme Tfl polymerase (Promega, Madison, Wis.). Uracil DNA Glycosylase (UDG, New England Biolabs, Beverly, Mass.) may also be used in the reaction buffer to prevent carryover. Two separate master mixes were prepared. Each contained reagents as above. Reverse transcriptase was added to one set of master mixes. Water in its place was added to the second set of master mix. Both of these mixes contained primers specific to the protease portion of a porcine endogenous retrovirus (PERV) (Patience et al., 1997 *Nature Medicine* Vol 3 Number 3).

C. Addition of Test and Control Articles to PCR Reaction Mixtures

Master mixes were aliquoted into numbered tubes. Tubes were then transported to the appropriate rooms for addition of test and control articles. Five to ten (1 of test or control article were added to each tube. Tubes were cross referenced by number and sample identification in the documentation. Test and control samples may be heated to 70° C. +/-2° C. for about 10 minutes to denature the RNA prior to adding to the reaction mixtures.

Reactions which contained protease-specific PERV primers and reverse transcriptase included the following test and control articles:

Master mix only-no template RNA
Negative control RNA from tobacco mosaic virus or other RNA virus, run in duplicate.
5–10 (1 of extracted and DNAse treated test article RNA(s).
Test article RNA or cocultivation indicator cell derived RNA spiked with at least the 10-2 dilution of positive control PERV RNA.
Extracted, DNAse treated RNA from positive control PERV stock in dilutions of at least $10^{-2}$, $10^{-3}$, $10^{-4}$.

Reactions which contained protease specific PERV primers without reverse transcriptase included one replicate of the following test and control articles:
Test article RNA(s)
Spiked test article RNA spiked or cocultivation indicator cell derived RNA.
Positive control RNA from the lowest dilution of PERV used in the assay D. Amplification, Gel Electrophoresis and Southern Transfer If UDG was added to the reaction mixtures the tubes were placed in a thermal cycler and incubated at 22° C. +/-2° C. to allow the UDG to act, then incubated at 95° C. +/-2° C. for 2 minutes prior to cDNA synthesis. cDNA synthesis occurred at 48° C. for 40–60 minutes. Reaction mixtures were then amplified through 35 to 40 cycles of denaturation, annealing and extension temperatures. Gel loading dye was added to the samples and the samples, along with DNA size standards, were electrophoresed on agarose gels. Ethidium bromide stained gels were observed and photographed on an UV transilluminator. Subsequent to gel staining, Southern transfer procedures were used to transfer samples amplified with the protease specific PERV primers to a nylon membrane. The membranes were UV crosslinked and, if not used immediately, wrapped and stored at 4° C. +/-2° C. until use.

E. Detection

The membranes were hybridized to a fluorescein-11-tagged oligonucleotide DNA probe. After washing and blocking, the membrane was incubated in a solution containing an antifluorescein-horseradish peroxidase conjugate. Signal generation and detection occurs with the addition of cherniluminescent detection solutions and subsequent exposure of the membrane to X-ray film.

Test System cDNAs were prepared from test article derived RNA. These cDNA were then analyzed by use of the polymerase chain reaction (PCR), followed by gel electrophoresis, Southern transfer, hybridization with an oligonucleotide probe and subsequent detection by chemiluminescence.

Control Articles
Positive Control Article
1. Identification: PERV RNA produced from PK-15 (ATCC # CCL-33) culture fluids
2. Source: GTC Washington Laboratories
3. Storage Conditions: -60° C. or below
Negative Control Article
1. Identification: RNA from Tobacco Mosaic Virus
2. Source: Boehringer Mannheim
3. Storage Conditions: -60° C. or below Assay Acceptance Criteria The assay is considered valid if the following results are obtained.

A. For reaction mixtures containing reverse transcriptase and amplified with PERV primers:
1. No signal is observed in either the no-template control or the negative control.
2. A signal is observed in at least the 10-2 dilution of the PK-15 supernatant derived PERV RNA.
3. A signal is observed in the test article or indicator cell derived RNA spiked with the 10-2 dilution of PERV positive control RNA.

B. For reaction mixtures which do not contain reverse transcriptase amplified with PERV primers:
I . No signal is observed in the negative control.
2. No signal is observed in the test article RNA(s).
3. No signal is observed in the positive control.

Detection of Porcine Endogenous Retroviral Reverse Transcriptase Activity

Objective

The objective of this assay is to determine whether retroviruses are present in the test 20 article by analysis for retroviral reverse transcriptase activity.

Experimental Design

Reverse transcriptase was determined using duplicate reactions. The incorporation of tritiated thymidine triphosphate into newly synthesized DNA was measured using a synthetic template, poly (rA)-oligo (dT). Porcine endogenous retrovirus virus (PERV) and monkey retrovirus (SMRV, ATCC VR-843) (type D) were included as positive controls. Test article samples were diluted with stabilization buffer and/or medium in order to determine if an inhibitor of reverse transcriptase activity is present. For the same purpose, test article samples were diluted with PERV. Reactions will contain Mn++ (for PERV) and Mg++ (for SMRV).
Assay Samples were as Follows
A. Undiluted test article
B. Test article diluted two-fold with stabilization buffer or medium
C. Test article diluted two-fold with PERV Mn++-dependent positive control)
D. PERV diluted two-fold with stabilization buffer or medium
E. SMRV (Mg++-dependent positive control)
F. Stabilization buffer and/or medium (negative control)
Rationale Retroviruses possess the enzyme RNA-dependent DNA polymerase (reverse transcriptase) which is capable of catalyzing the synthesis of DNA using retroviral RNA as a template. The endpoint the assay utilizes is the quantitation of incorporated tritiated thymidine triphosphate into newly synthesized DNA.
Protocol The assays were performed as described in Phan-Thanh et al. Porcine Retrovirus Reverse Transcriptase Optimal Conditions for its Determination. *Develop. Biol. Standard* 72, 111–116, 1990.
Results Data presented here are from the day 35 reverse transcriptase (RT) analysis and the day 42 RTPCR on cell free supernatants.

Monocultures and cocultivations were cultured for 35 days. At day 21 cell free supernatants were inoculated onto polybrened, subconfluent 293 monocultures (blind passage). Blind passage cultures were maintained for 21 days. Cells were harvested at day 35 of the cocultivation and day 21 of the blind passage. Day 21 of the blind passage is referred to as day 42 in this study. Cell free supernatants were harvested at days 7 and 35. Irradiated and unirradiated PBMC monocultures were harvested prior to day 21, consequently these two treatments were not blind passaged and no day 35 samples were available for these two treatments.

Figure 4:
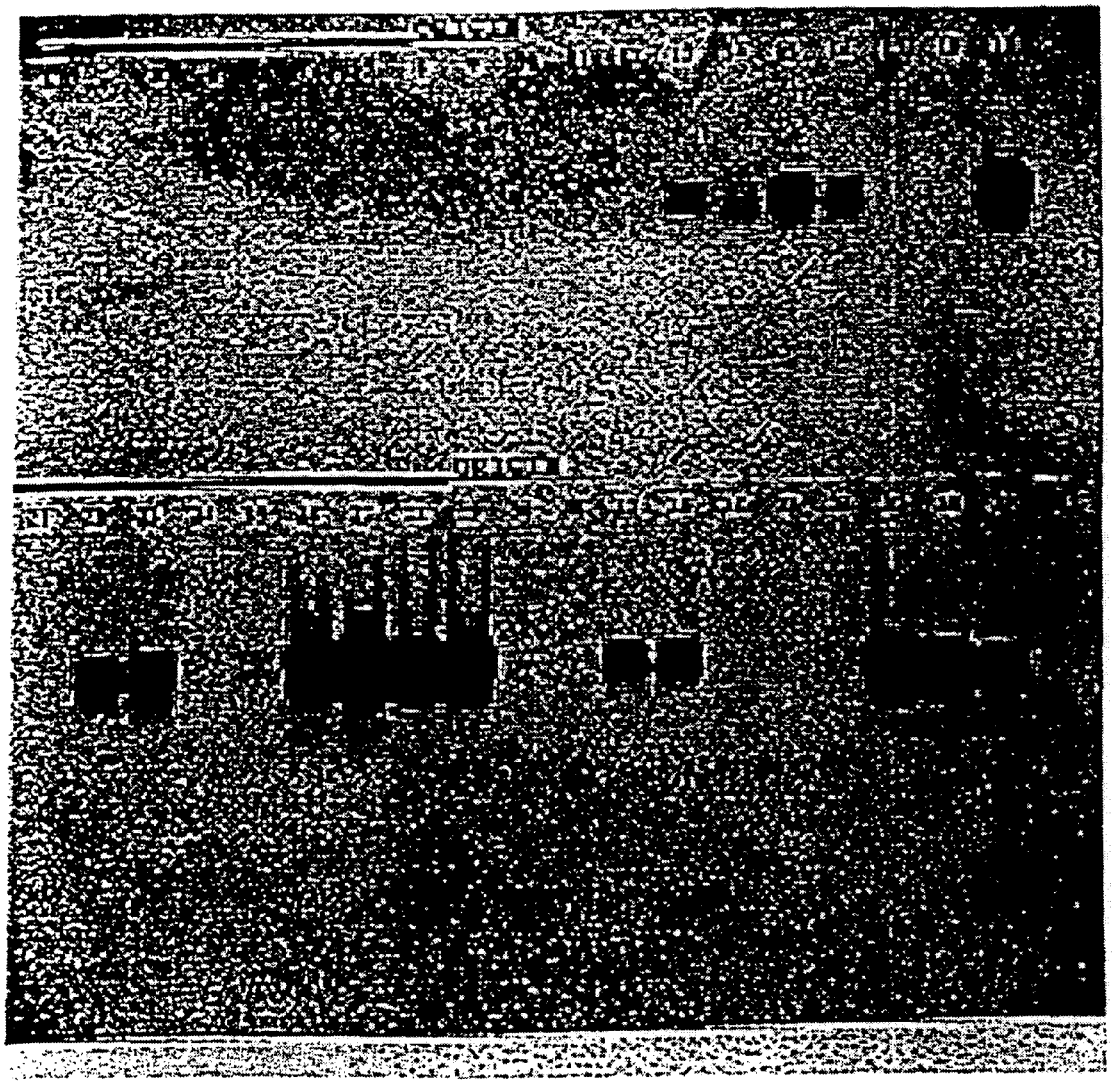
FIG. 4 is a depiction of hybridization of RT-PCR Amplified Reaction Products with a PERV Specific Oligonucleotide: Day 42 Cell Free Supernatants. Lane # Sample:
1 DNA size markers;
2. No template control;
3 Negative control;
4 Negative control;
5 293->293;
6 293->293;
7 ST Iowa->293;
8 ST Iowa->293;
9 Non-irradiated PBMCs/293->293;
10 Non-irradiated PBMCs/293->293;
11 Irradiated PBMCs/293->293;
12 Irradiated PBMCs/293->293;
13 Non-irradiated PBMCs/ST Iowa->293;
14 Non-irradiated PBMCs/ST Iowa->293;
15 Irradiated PBMCs/ST Iowa->293;
16 Irradiated PBMCs/ST Iowa->293;
17 Empty;
18 Empty;
19 2700 PERV virus particles;
20 Empty;
21 DNA size markers;
22 PK-15 monoculture->293;
23 PK-15 monoculture->293;
24 293 inoculated with PERV->293;
25 293 inoculated with PERV->293;
26 Irradiated PK-15/293->293;
27 Irradiated PK-15/293->293;
28 Irradiated PK-15/293->293;
29 Irradiated PK-15/293->293;
30 Empty;
31 Empty;
32 293->293 spiked with 27;00 vp;
33 293->293 spiked with 2700 vp;
34 293->293 spiked with 270 vp;
35 293->293 spiked with 270 vp;
36 Empty;
37 2700 PERV virus particles;
38 270 PERV virus particles;
39 27 PERV virus particles;
Empty

RNAs extracted from filtered and clarified day 42 cell supernatants were transcribed into cDNAs and then amplified with primers specific for porcine endogenous retrovirus (PERV) sequences. Following RT-PCR, reaction mixtures were transferred to a nylon membrane and hybridized with a PERV specific oligonucleotide. FIG. 4 shows the results of RT-PCR analysis of cell free supernatants derived from 293 cultures from day 21 of the blind passage. No evidence of PERV specific RNA was seen in supernatants from 293 cultures inoculated with supernatants derived from ST Iowa cells, 293 cells or irradiated and non-irradiated PBMCs cocultivated with 293 cells. PERV specific RNA was observed in supernatants from 293 cultures inoculated with supernatants derived from irradiated PBMC/ST Iowa cocultivations and to non-irradiated PBMC/ST Iowa cocultivations. PERV specific RNA was also observed in PK-15 cells alone and 293 cells cocultivated with PK-15 cells that had been irradiated at two different doses of radiation. A positive signal was also observed in one of two replicates of 293 cells inoculated with supernatants from PERV infected 293 cells. Positive signals were observed in 293 cells inoculated with day 35 293 culture supernatants spiked with 2700 virus particles. Positive controls equivalent to 2700 virus particles (vp)/reaction and 270 vp/reaction and 27 vp/reaction resulted in positive signals.

Table 8 shows the results of enzymatic reverse transcriptase (RT) analysis of day 35 cell free supernatants. No evidence of RT activity was seen in supernatants derived from indicator 293 cells alone or with 293 cells cocultivated with PBMCs or irradiated PBMCs.

TABLE 8

| Reverse Transcriptase Activity[1] | |
|---|---|
| Non-irradiated PBMC/293 | 560[c] |
| Diluted 2-fold with buffer | 515 |
| Diluted 2-fold with PERV | 47,864 |
| Irradiated PBMC/293 | 514 |
| Non-irradiated PBMC/ST Iowa | 20,659 |
| Diluted 2-fold with buffer | 11,139 |
| Diluted 2-fold with PERV | 68,221 |
| Irradiated PBMC/ST Iowa | 20,447 |
| 293 | 327 |
| ST Iowa | 1258[a] |
| Irradiated PK- 15/293 | 33,995 |
| Diluted 2-fold with buffer | 7322 |
| Diluted 2-fold with PERV | 56,630 |
| Irradiated PK-15/293 | 33,541 |
| PK-15 | 4713 |
| 293 inoculated with PERV | 493 |
| PERV diluted 2-fold with buffer | 28,239 |
| Stabilization buffer | 573[b] |

[1]Mn++ dependent reverse transcriptase activity. Mean of duplicate samples from one culture.
Mean deviations are 10% or less except as follows: [a]31%; [b]18%; [c]16%.

When PBMCs were cocultivated with ST Iowa cells, levels or incorporation of 3H-TTP were 16 times greater than with ST Iowa cells alone. When irradiated PK-15 cells were cocultivated with 293 cells, the reverse transcriptase activity was at least seven times greater than with non-irradiated PK-15 cells alone, indicating that either 293 cell were infected and PERV was amplified, or that the PK-15 cells had a greater capacity for infection as a result of experimental conditions such as irradiation. No inhibition of PERV positive control was observed when cocultivated cells were diluted with PERV.

These results are in contrast to the results of Wilson et al. (1998, *J. Virology* vol 72, no. 4: 3082–3087) which reported that mitogenic activation of PBMC from the National Institutes of Health (NIH) minipig and the Yucatan pig resulted in the activation and releae of an infectious type C retrovirus. Coculture of activated porcine PBMC with pig and human cell lines using the NIH minipig or the Yucatan pig resulted in the transfer and expression of PERV-specific sequences and the establishment of a productive infection (Wilson et al. 1998, *J. Virology* vol 72, no. 4: 3082–3087).

Example 4

Microsatellite Analysis of Inbred Miniature Swine

Recently, mapping of microsatellite polymorphisms in mice and domestic livestock animals has generated genetic maps which can be used for marker assisted selection of breeding pairs. In mouse, this has facilitated rapid construction of congenic inbred strains. In livestock, this has been employed to speed the process of generating strains with commercially important traits. Additionally, microsatellite markers can be used to rapidly detect recombination events (e.g. with the MHC complex) and to distinguish animals at an early stage (e.g., in embryo/fetal populations).

Short Tandem Repeats (STR's) are efficient tools for mapping specific traits or to follow the flow of genetic material in a population. The technology is based on the presence of short tracks of di, tri, tetra or penta nucleotide repeats which are common in the genomes of eukaryotic organisms. These short tracks (5 to 10 repeating units) are faithfully transmitted thought sexual reproduction, but are often highly polymorphic within a population.

High-throughput analysis of STR loci can be performed by first amplifying the loci using flanking PCR primers. The size of loci (and hence the characteristic number of repeats) can be identified following electrophoretic separation on an ABI 377 sequence detector, provided fluorescent primers are used to tag the amplified products.

A pilot study of swine microsatellite markers in a highly inbred pair of miniature swine has been performed. Genomic DNA was isolated from miniature swine #s 13220 and 13222 (inbred at the SLA haplotype). Using 225 pairs of primers (obtained from Professor Max Rothschild, Iowa State University, Ames Iowa) PCR products were generated. The PCR products were sized and analyzed by Lark Technologies Inc. (Houston, Tex.). The results of the genotype analysis are presented in Table 9.

TABLE 9

Genotype Analysis

|  | Miniature swine #13220 | Miniature swine #13222 |
| --- | --- | --- |
| Number of different primer pairs used in the PCR assay | 225 | 225 |
| Number of different primer pairs that gave rise to PCR products | 196 | 197 |
| Number (%) of different primer pairs that resulted in PCR products of the same length and as such, were considered to correspond to monomorphic alleles | 126 (64%) | 147 (74%) |
| Number (%) of different primer pairs that resulted in PCR products of different lengths and as such, were considered to correspond to dimorphic alleles | 70 | 50 |
| Number (%) of different primer pairs that resulted in PCR products of different lengths and as such, were considered to correspond to dimorphic alleles present in both animals | 41*** | 41 |
| Number (%) of different primer pairs that resulted in PCR products of different lengths and as such, were considered to correspond to dimorphic alleles different in the two animals | 29* | 9** |

*This number contains 13 loci with alleles differing by 2–3 bp
**This number contains 2 loci with alleles differing by 2–3 bp
***This number contains 16 loci with alleles differing by 2–3 bp.

As analysis of alleles that differ by 2–3 bp needs to be interpreted with some caution further analysis should be performed to ascertain whether the alleles are monomorphic or dimorphic. These results therefore indicate the minimum extent of inbreeding. Using these results, however, it can be determined that the coefficiency of inbreeding for miniature swine #s 13220 and 13222 are 0.64 and 0.74, respectively.

These analyses provide a rationale for the inbreeding program in the selection of animals to maximize the extent of inbreeding.

Other Embodiments

The methods of the invention are particularly useful for replacing a tissue or organ afflicted with a neoplastic disorder, particularly a disorder which is resistant to normal modes of therapy, e.g., chemotherapy or radiation therapy. In preferred embodiments: the graft includes tissue from the digestive tract or gut, e.g., tissue from the stomach, or bowel tissue, e.g., small intestine, large intestine, or colon; the graft replaces a portion of the recipient's digestive system e.g., all or part of any of the digestive tract or gut, e.g., the stomach, bowel, e.g., small intestine, large intestine, or colon.

Methods of the invention minimize or eliminate the need for preparative WB irradiation. However, when irradiation is administered, it is possible to induce mixed chimerism with less radiation toxicity by fractionating the radiation dose, i.e., by delivering the radiation in two or more exposures or sessions. Accordingly, in any method of the invention calling for the irradiation of a recipient, e.g., a primate, e.g., a human, recipient, of a xenograft, the radiation can either be delivered in a single exposure, or more preferably, can be fractionated into two or more exposures or sessions. The sum of the fractionated dosages is preferably equal, e.g., in rads or Gy, to the radiation dosage which can result in mixed chimerism when given in a single exposure. The fractions are preferably approximately equal in dosage. Hyperfractionation of the radiation dose can also be used in methods of the invention. The fractions can be delivered on the same day, or can be separated by intervals of one, two, three, four, five, or more days. Whole body irradiation, thymic irradiation, or both, can be fractionated.

Thymic irradiation can also be fractionated. For example, a single dose of 700 rads can be replaced with, e.g., two fractions of 350 rads, or seven fractions of 100 rads.

Methods of the invention can include recipient splenectomy.

As is discussed herein, hemoperfusion, e.g., hemoperfusion with a donor organ, can be used to deplete the host of natural antibodies. Other methods for depleting or otherwise inactivating natural antibodies can be used with any of the methods described herein. For example, drugs which deplete or inactivate natural antibodies, e.g., deoxyspergualin (DSG) (Bristol), or anti-IgM antibodies, can be administered to the recipient of an allograft or a xenograft. One or more of, DSG (or similar drugs), anti-IgM antibodies, and hemoperfusion, can be used to deplete or otherwise inactivate recipient natural antibodies in methods of the invention. DSG at a concentration of 6 mg/kg/day, i.v., has been found useful in suppressing natural antibody function in pig to cynomolgus kidney transplants.

In any of the methods described herein, particularly primate or clinical methods, it is preferable to form mixed chimerism as opposed to entirely replacing the recipient's stem cells with donor cells.

Any of the methods referred to herein can include the administration of agents, e.g., 15-deoxyspergualin, mycophenolate mofetil, brequinar sodium, or similar agents, which inhibit the production, levels, or activity of antibodies in the recipient. One or more of these agents can be administered: prior to the implantation of donor tissue, e.g., one, two, or three days, or one, two, or three weeks before implantation of donor tissue; at the time of implantation of donor tissue; or after implantation of donor tissue, e.g., one, two, or three days, or one, two or three weeks after, implantation of a graft.

Preferred embodiments include administration of 15-deoxyspergualin (6 mg/kg/day) for about two weeks beginning on the day of graft implantation.

Some of the methods referred to herein include the administration of hematopoietic stem cells to a recipient. The inventors have found that administration of one or more cytokines, preferably a cytokine from the species from which the stem cells are derived, can promote engraftment, mixed chimerism, and tolerance, or otherwise prolong acceptance of a graft. The use of such cytokines can reduce or eliminate the need for whole body irradiation. Thus, the invention also includes methods in the recipient is administered one or more cytokine, e.g., a donor-species cytokine.

Although not wishing to be bound by theory, the inventors believe that the cytokines, particularly donor species cytokines, promote the engraftment and/or function of donor stem cells or their progeny cells. Accordingly, any method referred to herein which includes the administration of hematopoietic stem cells can further include the administration of a cytokine, e.g., SCF, IL-3, or GM-CSF. In preferred embodiments the cytokine one which is species specific in its interaction with target cells.

Administration of a cytokine can begin prior to, at, or after the implantation of a graft or the implantation of stem cells.

The method can further include the step of administering a first or subsequent dose of a cytokine to the recipient: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft. Thus, method of the invention can be modified to include a further step of determining if a subject is in need of cytokine therapy and if so, administering a cytokine.

The period over which the cytokine(s) is administered (or the period over which clinically effective levels are maintained in the subject) can be long term, e.g., for six months of more or a year or more, or short term, e.g., for a year or less, more preferably six months or less, more preferably one month or less, and more preferably two weeks or less. The period will generally be at least about one week and preferably at least about two weeks in duration.

In preferred embodiments the recipient is a primate, e.g., a human, and the donor is from a different species, e.g., the donor is a pig and: pig SCF is administered; pig IL-3 is administered; a combination of pig SCF and pig IL-3 is administered; a pig specific hematopoiesis enhancing factor, e.g., pig GM-SCF, is administered, e.g., after the implantation of stem cells, e.g., about a month after the implantation of stem cells.

A particularly preferred embodiment combines a short course, e.g., about a month, of cyclosporine or a similar agent, a short course, e.g., about two weeks, of 15-deoxyspergualin or a similar agent, and a short course, e.g., about two weeks, of donor specific cytokines, e.g., SCF and IL-3. In Cynomolgus monkeys receiving pig grafts and pig stem cells, treatment which included the combination of cyclosporine (15 mg/kg/day for 28 days), 15-deoxyspergualin (6 mg/kg/day for two weeks), and recombinant pig cytokines (SCF and IL-3, each at 10 µg/kg/day, i.v., for two weeks) was found to be useful. Administration began at the time of graft implant. (The monkeys were also given a preparative regime consisting of 3×100 cGy whole body irradiation on day -6, and -5 and hemoperfusion with a pig liver just prior to stem cell administration.)

An anti-CD2 antibody, preferably a monoclonal, e.g., BTI-322, or a monoclonal directed at a similar or overlapping epitope, can be used in addition to or in place of any anti-T cell antibodies (e.g., ATG) in any method referred to herein.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for providing a swine which is homozygous at swine leukocyte antigens (SLA) A, B, C, DR, and DQ, and in which at least 60% of all other genetic loci are homozygous, comprising:

providing a first swine which is homozygous at swine leukocyte antigens (SEA) A, B, C, DR, and DQ but which is homozygous at less than 60% of all other loci;
(1) providing a second swine which is homozygous at swine leukocyte antigens (SLA) A, B, C, DR, and DQ, which is of the same haplotype as the first swine, but which is homozygous at less than 60% of all other loci, which is not a sibling, parent or offspring of the first swine;
(2) mating said first and second swine to provide an offspring;
(3) mating said offspring to a swine which is homozygous at swine leukocyte antigens (SLA) A, B, C, DR, and DQ, which is of the same haplotype as the first swine but which is homozygous at less than 60% of all other loci, which is preferably not a sibling, parent or offspring of the offspring;
(4) repeating step (3) for at least 18 generations;
(5) performing a brother sister mating from the offspring of the final mating of step (4) to produce at least one male and one female sibling; and
(6) performing brother sister matings from the siblings of step (5) and for at least 5 additional generations, thereby providing a swine which is homozygous at swine leukocyte antigens (SLA) A, B, C, DR, and DQ, and in which at least 60% of all other genetic loci are homozygous.

2. A swine made by the method of claim 1.

* * * * *